US010687494B2

(12) United States Patent
De Groot et al.

(10) Patent No.: US 10,687,494 B2
(45) Date of Patent: Jun. 23, 2020

(54) WATERMELON PLANTS WITH CUCUMBER VEIN YELLOWING VIRUS (CVYV) RESISTANCE

(71) Applicant: NUNHEMS B.V., Nunhem (NL)

(72) Inventors: Erik De Groot, Nonantola (IT); Marion Van De Wal, Best (NL); Richard Bernard Berentsen, Zutphen (NL); Elena Chiapparino, Bologna (IT); Ebenezer Ogundiwin, Woodland, CA (US)

(73) Assignee: NUNHEMS B.V., Nunhem (NL)

( * ) Notice: Subject to any disclaimer, the term of this patent is extended or adjusted under 35 U.S.C. 154(b) by 99 days.

(21) Appl. No.: 15/766,220

(22) PCT Filed: Oct. 6, 2016

(86) PCT No.: PCT/EP2016/073875
§ 371 (c)(1),
(2) Date: Apr. 5, 2018

(87) PCT Pub. No.: WO2017/060350
PCT Pub. Date: Apr. 13, 2017

(65) Prior Publication Data
US 2018/0310514 A1    Nov. 1, 2018

(30) Foreign Application Priority Data
Oct. 6, 2015  (EP) .................................... 15188630

(51) Int. Cl.
*A01H 6/34* (2018.01)
*A01H 5/08* (2018.01)
*A01H 1/04* (2006.01)

(52) U.S. Cl.
CPC .............. *A01H 6/342* (2018.05); *A01H 1/04* (2013.01); *A01H 5/08* (2013.01)

(58) Field of Classification Search
CPC ...................................................... A01H 5/08
See application file for complete search history.

(56) References Cited

U.S. PATENT DOCUMENTS

2011/0214202 A1   9/2011   Kassies et al.
2012/0137388 A1   5/2012   Mazereeuw et al.

FOREIGN PATENT DOCUMENTS

WO    WO 2010/025747 A1    3/2010
WO    WO 2011/033440 A1    1/2011
WO    WO 2012/069539 A1    5/2012

OTHER PUBLICATIONS

Kousik, Chandrasekar S., et al. "Sources of resistance in US plant introductions to watermelon vine decline caused by squash vein yellowing virus." HortScience 44.2 (2009): 256-262. (Year: 2009).*
Mauricio, Rodney. "Mapping quantitative trait loci in plants: uses and caveats for evolutionary biology." Nature Reviews Genetics 2.5 (2001): 370-381. (Year: 2001).*
Gillaspie Jr, A. G., and J. M. Wright. "Evaluation of *Citrullus* sp. germ plasm for resistance to watermelon mosaic virus 2." Plant disease 77.4 (1993): 352-354. (Year: 1993).*
Gillaspie Jr, A. G., and J. M. Wright. "Evaluation of *Citrullus* sp. germ plasm for resistance to watermelon mosaic virus 2." Plant disease 77.4 (1993): 352-354. (Year: 1993).*
2007 OEPP/EPPO Bulletin 37, pp. 554-559, entitled "Cucumber vein yellowing virus (Ipomovirus)".
Allen et al., "Transcript-specific, single-nucleotide polymorphism discovery and linkage analysis in hexaploid bread wheat (*Triticum aestivum* L.)", Plant Biotechnology, 2011, vol. 9, pp. 1086-1099.
D.N. Maynard et al., Triploid Watermelon Production Practices and Varieties, XP-002966111, 1992, pp. 169-173.
Eigsti, "Environmental factors in vegetable production", Hort Science, 1971, vol. 6, No. 1, pp. 1-2.
Guner et al. "The Genes of Watermelon", Hort Science, 2004, vol. 39, No. 6, pp. 1175-1182.
Guo et al., "The draft genome of watermelon (*Citrullus lanatus*) and resequencing of 20 diverse accessions", Nature Genetics, 2013, vol. 45, No. 1, pp. 51-58.
Henikoff et al., "Amino Acid Substitution Matrices from Protein Blocks", Proc. Natl. Acad. Sci., 1992, vol. 89, pp. 10915-10919.
Kihara, "Triploid Watermelons", Proceedings of American Society for Horticultural Science, 1951, vol. 58, pp. 217-230.
Ling et al., "Identification of a CAPS marker in an eIF4E gene linked to Zucchini yellow mosaic virus resistance in watermelon", (Cucurbitaceae 2008, Proceeding of the IXth Eucarpia Meeting, May 21-24).
Noh et al., Screening Different Methods of Tetraploid Induction in Watermelon [*Citrullus lanatus* (thunb.) Manst. and Nakai], Hort. Environ. Biotechnol., 2012, vol. 53, No. 6, pp. 521-529.
Sari et al., "Comparison of ploidy level screening methods in watermelon: *Citrullus lanatus* (Thunb.) Matsum. and Nakai", Scientia Horticulturae, 1999, vol. 82, pp. 265-277.
Seedless Watermelon Breeding, Cucurbit Breeding at NC State, last accessed Mar. 1, 2018, 4 pages.
International Search Report issued in International Patent Application No. PCT/EP2016/073875, dated Dec. 15, 2016 (2 pages).

* cited by examiner

*Primary Examiner* — Lee A Visone
(74) *Attorney, Agent, or Firm* — Arent Fox LLP

(57) ABSTRACT

The application relates to the field of plant breeding, in particular watermelon breeding. Provided are CVYV resistant watermelon plants (and seeds from which these plants can be grown). Also provided is a QTL for CVYV resistance (cyv_3.1) and markers and methods for screening plants for the presence of the QTL.

23 Claims, 1 Drawing Sheet
Specification includes a Sequence Listing.

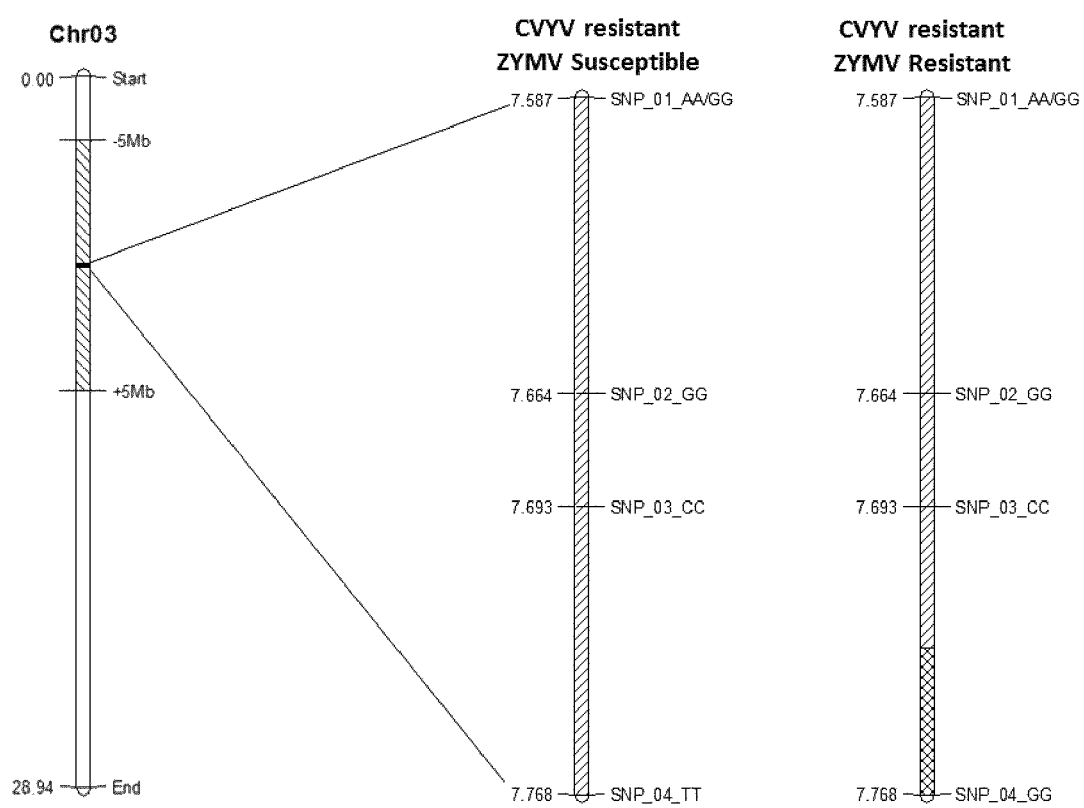

SEQUENCE LISTING

```
<160> NUMBER OF SEQ ID NOS: 4

<210> SEQ ID NO 1
<211> LENGTH: 151
<212> TYPE: DNA
<213> ORGANISM: Citrullus lanatus
<220> FEATURE:
<221> NAME/KEY: SNP01
<222> LOCATION: (76)..(76)
```

```
<400> SEQUENCE: 1
ggggcgaata aaataaaata aataaatttg gtagggttgg agtggaataa aggagatttt      60
attttatttg gttgaagaaa caaaaaggga aaaattggaa ttaagggttt aaggagggag     120
aggaattagg gtttagttta atcccaccct c                                   151

<210> SEQ ID NO 2
<211> LENGTH: 151
<212> TYPE: DNA
<213> ORGANISM: Citrullus lanatus
<220> FEATURE:
<221> NAME/KEY: SNP02
<222> LOCATION: (76)..(76)

<400> SEQUENCE: 2
tcagtcatag tatagtggaa tatttgactg caggtataag actcaacttc agaaagatcc      60 agacctttt tttaagagag agagagagag agagagagag agaactagaa acaacaattt     120
ccaccaaaag aatgaaaaga gactaagact c                                   151

<210> SEQ ID NO 3
<211> LENGTH: 151
<212> TYPE: DNA
<213> ORGANISM: Citrullus lanatus
<220> FEATURE:
<221> NAME/KEY: SNP03
<222> LOCATION: (76)..(76)

<400> SEQUENCE: 3
cgagttggct attagagttg atcgttggag atgattgact gagttagttg ctagaggtgg      60
tcgttgagtt ggttgccgaa ggtattcgtc agggctagtt gcgaagttgg gctttggaga    120
agtggagata gtcattgtag ttgattgatg g                                   151

<210> SEQ ID NO 4
<211> LENGTH: 340
<212> TYPE: DNA
<213> ORGANISM: Citrullus lanatus
<220> FEATURE:
<221> NAME/KEY: SNP04
<222> LOCATION: (70)..(70)

<400> SEQUENCE: 4
tgaagttcta cctccaaaac tcctcaacag tagagaaggt atagatcggt cggatagacg      60
cacccagggg ggcttgctta gacttggcgg atgggttatc gaaccaaaag gtccaagagt    120
gctcaagagg gtgaggctga tgcactatcg ccgccgacaa attggacgag tcaaggtcgt    180
cgtctccgac gatctctcct tcctcaagtt cctcatcttc atcaccgcct cgtcctctag    240
ggttttgatt tgcaatggta ttagaaagat cttccgtgga tgtagctttg atcgtctctt    300
cgactaccat tttcctttca ctacttgtgg aattgagcgt                          340
```

US 10,687,494 B2

1

WATERMELON PLANTS WITH CUCUMBER VEIN YELLOWING VIRUS (CVYV) RESISTANCE

CROSS REFERENCE TO RELATED APPLICATIONS

This application is a 35 U.S.C. 371 National Phase of PCT Application No. PCT/EP2016/073875 filed Oct. 6, 2016, which claims benefit to EP Application No. 15188630.6 filed Oct. 6, 2015, the disclosure of which is hereby incorporated by reference in its entirety.

FIELD OF THE INVENTION

The present invention relates to the field of plant breeding and plant improvement. Provided are Cucumber Vein Yellowing Virus (CVYV) resistant watermelon plants and SNP (Single Nucleotide Polymorphism) markers tightly linked to the CVYV resistance locus. These markers can be used to select watermelon plants, or plant parts, that comprise the CVYV resistance locus and are CVYV resistant when the resistance locus is in homozygous form in a diploid plant, or in three or four copies in a triploid or tetraploid respectively. The markers can also be used to distinguish plants (or plant parts from such plants) comprising the CVYV resistance locus from plants (or plant parts) lacking the CVYV resistance locus. The CVYV resistance locus is a single recessive locus. The locus is located on chromosome 3 of the watermelon genome. On the same chromosome Ling et al. (Cucurbitaceae 2008, Proceedings of the IXth Eucarpia Meeting, May 21-24) reported a marker in the eIF4E gene to be linked to ZYMV (Zucchini Yellow Mosaic Virus) resistance conferred by a recessive gene called zym. The cultivated watermelon plants of the invention, comprising a homozygous introgression from wild watermelon conferring CVYV resistance, did not comprise ZYMV resistance and did not comprise the marker in the eIF4E gene reported by Ling et al. 2008 (supra). The CVYV resistance locus of the invention can, therefore, be used alone, or it can optionally be combined with ZYMV resistance (the recessive zym gene), to produce double resistant plants. The watermelon plants of the invention, comprising an introgression fragment on chromosome 3, are cultivated plants of *C. lanatus* ssp. *vulgaris* which produce marketable fruits with a degree brix of at least 8.0 or 9.0, preferably at least 10.0, or at least 11.0. The plants or plant parts thus comprise a genome of cultivated watermelon (*C. lanatus* ssp. *vulgaris*), which comprises an introgression fragment of a wild watermelon on chromosome 3 (either of a plant of the species *C. lanatus* ssp. *lanatus* or of a plant of the species *C. lanatus* ssp. *mucosospermus*), whereby said introgression fragment comprising the CVYV-resistance locus. The CVYV locus and/or introgression fragment can be identified in the cells, plants, plant parts or DNA thereof by tightly linked markers, i.e. by the SNP genotype (or SNP haplotype) of one or more of the SNP-markers provided herein.

BACKGROUND OF THE INVENTION

CVYV is a potyvirus (family Potyviridae) which causes severe damages in cucurbits, such as cucumber, melon, watermelon and zucchini. The virus can be transmitted mechanically and by the natural vector for CVYV, which is the whitefly *Bemisia tabaci*. The whitefly vector *B. tabaci* is endemic in many of the world's main watermelon growing areas. CVYV infects both crops in the field, as well as in plastic tunnels.

Resistance against CVYV has been identified in melon and cucumber, but not yet in watermelon. For example WO2010/025747 describes a resistance QTL against CVYV in melon, derived from landrace Cuc6491. WO2011003440 describes CVYV resistance in cucumber.

Symptoms of CVYV in watermelon are sometimes mild leaf chlorosis, but often external symptoms are inconspicuous or not expressed. CVYV infection is then only seen when fruits are found to have developed internal necrosis not seen from the outside, but which makes the fruits unsuitable for consumption.

Identification of CVYV is possible by reverse transcriptase PCT (RT-PCR) and by nucleic acid hybridization, as for example described in the 2007 OEPP/EPPO Bulletin 37, pp 554-559, entitled "Cucumber vein yellowing virus (Ipomovirus)". This document also describes mechanical and whitefly transmissions to test plants for identifying CVYV.

It is an object of the invention to provide cultivated watermelon plants, *C. lanatus* ssp. *vulgaris*, and parts of such plants, comprising a resistance locus on chromosome 3, which confers resistance against CVYV when in homozygous form in a diploid plant, or when in three or four copies in a triploid or tetraploid plant respectively. This locus is a Quantitative Trait Locus (QTL) identified in two different wild accession of *Citrullus lanatus* ssp. *lanatus* and *Citrullus lanatus* ssp. *mucosospermus*, which have white-fleshed or yellow fleshed fruits that are bitter tasting and have a very low brix (e.g. a brix of 3.0 or less), and this locus was introgressed into cultivated watermelon (*Citrullus lanatus* ssp. *vulgaris*) having marketable fruits, i.e. fruits of good quality with a brix of at least 8.0 or 9.0 or preferably at least 10.0, 11.0 or higher. This CVYV resistance-conferring QTL is herein referred to as cyv_3.1.

The cultivated watermelon plants comprising cyv_3.1 in one, two, three or four copies include diploid plants or doubled-haploid plants, tetraploid plants and triploid plants (e.g. triploid hybrid plants producing seedless fruits), as well as seeds from which these plants can be grown, and any parts of the plants comprising the cyv_3.1 (fruits, fruit parts, root stocks, scions, cells, pollen, anthers, ovules, stems, leaves, cotyledons, hypocotyls, flowers, in vitro cell or tissue cultures, in vitro propagations, etc.).

It is also an object of the invention to provide molecular markers closely linked to the CVYV resistance conferring QTL cyv_3.1 and the use of one or more of such molecular markers in a) breeding cultivated watermelon plants comprising cyv_3.1 in one (e.g. heterozygous in a diploid), two (e.g. homozygous in diploid and doubled-haploid plants), three (in a triploid) or four copies (in a tetraploid) and/or b) screening plants, plant parts, cells or genomic DNA for the presence of one or more of these molecular markers and thereby for the presence of cyv_3.1. Such breeding methods and screening methods are encompassed herein.

General Definition

The verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one", e.g. "a plant" refers also to several cells plants, etc. Similarly, "a fruit" or "a plant" also refers to a plurality of fruits and plants.

As used herein, the term "plant" includes the whole plant or any parts or derivatives thereof, preferably having the same genetic makeup as the plant from which it is obtained, such as plant organs (e.g. harvested or non-harvested fruits, leaves, flowers, anthers, etc.), plant cells, plant protoplasts, plant cell tissue cultures from which whole plants can be regenerated, plant calli, plant cell clumps, plant transplants, seedlings, plant cells that are intact in plants, plant clones or micropropagations, or parts of plants, such as plant cuttings, embryos, pollen, anthers, ovules, fruits (e.g. harvested tissues or organs), flowers, leaves, seeds, clonally propagated plants, roots, stems, root tips, grafts (scions and/or root stocks) and the like. Also any developmental stage is included, such as seedlings, cuttings prior or after rooting, etc. When "seeds of a plant" are referred to, these either refer to seeds from which the plant can be grown or to seeds produced on the plant, after self-fertilization or cross-fertilization.

As used herein, the term "variety" or "cultivar" means a plant grouping within a single botanical taxon of the lowest known rank, which can be defined by the expression of the characteristics resulting from a given genotype or combination of genotypes.

The term "allele(s)" means any of one or more alternative forms of a gene at a particular locus, all of which alleles relate to one trait or characteristic at a specific locus. In a diploid cell of an organism, alleles of a given gene are located at a specific location, or locus (loci plural) on a chromosome. One allele is present on each chromosome of the pair of homologous chromosomes. A diploid plant species may comprise a large number of different alleles at a particular locus. These may be identical alleles of the gene (homozygous) or two different alleles (heterozygous).

"F1, F2, F3, etc." refers to the consecutive related generations following a cross between two parent plants or parent lines. The plants grown from the seeds produced by crossing two plants or lines is called the F1 generation. Selfing the F1 plants results in the F2 generation, etc.

"F1 hybrid" plant (or F1 hybrid seed) is the generation obtained from crossing two inbred parent lines. Thus, F1 hybrid seeds are seeds from which F1 hybrid plants grow. F1 hybrids are more vigorous and higher yielding, due to heterosis. Inbred lines are essentially homozygous at most loci in the genome.

A "plant line" or "breeding line" refers to a plant and its progeny. As used herein, the term "inbred line" refers to a plant line which has been repeatedly selfed and is nearly homozygous. Thus, an "inbred line" or "parent line" refers to a plant which has undergone several generations (e.g. at least 5, 6, 7 or more) of inbreeding, resulting in a plant line with a high uniformity.

The term "gene" means a (genomic) DNA sequence comprising a region (transcribed region), which is transcribed into a messenger RNA molecule (mRNA) in a cell, and an operably linked regulatory region (e.g. a promoter). Different alleles of a gene are thus different alternatives form of the gene, which may be in the form of e.g. differences in one or more nucleotides of the genomic DNA sequence (e.g. in the promoter sequence, the exon sequences, intron sequences, etc.), mRNA and/or amino acid sequence of the encoded protein.

The term "locus" (loci plural) means a specific place or places or a site on a chromosome where for example a QTL, a gene or genetic marker is found. The CVYV locus (or CVYV resistance conferring locus) is, thus, the location in the genome of watermelon, where the QTL named cyv_3.1 is found. The cyv_3.1 locus is introgressed into cultivated watermelon chromosome 3 (using the chromosome assignment of the published watermelon genome found at http://www.icugi.org/cgi-bin/ICuGI/index.cgi under "Watermelon: Genome", "Watermelon genome (97103)—version 1" and as described in Guo S, Zhang J, Sun H, Salse J, Lucas W, Zhang H, Zheng Y, Mao L, Ren Y, Wang Z (2013) "The draft genome of watermelon (*Citrullus lanatus*) and resequencing of 20 diverse accessions" (Nature Genetics 45:51-58) i.e. cyv_3.1 is introgressed into the cultivated watermelon genome (i.e. onto chromosome 3) from a wild watermelon.

A "quantitative trait locus", or "QTL" is a chromosomal locus that encodes for one or more alleles that affect the expressivity of a continuously distributed (quantitative) phenotype. The CVYV resistance conferring quantitative trait locus (or "CVYV QTL") is named cyv_3.1 herein.

"Diploid plant" refers to a plant, vegetative plant part(s), or seed from which a diploid plant can be grown, having two sets of chromosome, designated herein as 2n.

A "DH plant" or "doubled-haploid plant" is a diploid plant produced by doubling the haploid genome of the diploid plant using e.g. in vitro techniques. A DH plant is, therefore, homozygous at all loci.

"Triploid plant" refers to a plant, vegetative plant part(s), or seed from which a triploid plant can be grown, having three sets of chromosomes, designated herein as 3n.

"Tetraploid plant" refers to a plant, vegetative plant part(s), or seed from which a tetraploid plant can be grown, having four sets of chromosomes, designated herein as 4n.

"Pollenizer plant" or "pollenizer" refers to the (inbred or hybrid) diploid plant, or parts thereof (e.g. its pollen or scion), suitable as pollenizer for inducing fruit set on triploid plants. A pollenizer plant is, thus, able to lead to good fruit set (and good triploid fruit yield) of triploid plants, by producing an appropriate amount of pollen at the appropriate day-time and for an appropriate period of time.

"Hybrid triploid plant" or "F1 triploid" or "triploid hybrid" is a triploid plant grown from hybrid, triploid seed obtained from cross fertilizing a male diploid parent with a female tetraploid parent. The male parent (the pollenizer plant) is used for inducing fruit set and seed production on a tetraploid female parent, resulting in fruits containing F1 hybrid triploid seeds. Both the male parent and the female parent used to produce F1 triploid seeds are inbred so that each parent line is nearly homozygous and stable.

"Seedless fruit" are triploid fruits, produced on a triploid plant after a pollinizer plant induces fruit set, which fruits contain no mature seeds. The fruit may contain one or more small, edible, white ovules.

"Interplanting" refers to the combination of two or more types of seeds and/or transplants sown or transplanted on the same field, especially the sowing and/or transplanting of pollenizers in the same field as triploid hybrid plants (for seedless fruit production on the triploid plants and diploid fruit production on the pollenizer plants). For example, the pollenizer may either be planted in separate rows or interplanted with the triploid plants in the same row (e.g. in hills within each row). Pollenizers may also be planted in between rows of triploids. Also seeds of pollenizers and triploid hybrids may be mixed prior to seeding, resulting in random seeding. The transplants of the triploid hybrid plants and/or pollenizer plants may also comprise a rootstock of a different plant. Suitable rootstocks are known in the art. Watermelon plants with a different rootstock are referred to as "grafted".

"Planting" or "planted" refers to seeding (direct sowing) or transplanting seedlings (plantlets) into a field by machine or hand.

"Vegetative propagation" or "clonal propagation" refers to propagation of plants from vegetative tissue, e.g. by in vitro propagation or grafting methods (using scions). In vitro propagation involves in vitro cell or tissue culture and regeneration of a whole plant from the in vitro culture. Grafting involves propagation of an original plant by grafting onto a rootstock. Clones (i.e. genetically identical vegetative propagations) of the original plant can thus be generated by either in vitro culture or grafting. "Cell culture" or "tissue culture" refers to the in vitro culture of cells or tissues of a plant. "Regeneration" refers to the development of a plant from cell culture or tissue culture or vegetative propagation. "Non-propagating cell" refers to a cell which cannot be regenerated into a whole plant.

"Recessive" refers to an allele which expresses its phenotype (e.g. CVYV resistance) when no dominant allele is present in the genome. The cyv_3.1 according to the invention results in a CVYV resistant plant when present in two copies in a diploid plant, in four copies in a tetraploid plant or in three copies in a triploid plant, whereby a dominant allele is absent in these plants. The dominant allele is herein referred to as the wild type (WT) allele, found in plants lacking the cyv_3.1 introgression.

"Cultivated watermelon" refers herein to *Citrullus lanatus* ssp. *vulgaris* and having good agronomic characteristics, especially producing marketable fruits of good fruit quality and fruit uniformity.

"Wild watermelon" refers herein to *Citrullus lanatus* ssp. *lanatus* and *Citrullus lanatus* ssp. *mucosospermus*, producing fruits of poor quality and poor uniformity.

"SNP marker" refers to a Single Nucleotide Polymorphism between cultivated and wild watermelon and the SNP markers provided herein are tightly linked to the cyv_3.1 found in CVYV resistant wild watermelon accessions. SNP_02 comprises a 'G' (Guanine) at nucleotide 7.664.093 of chromosome 3 instead of an 'A' (Adenine) and SNP_03 comprises a 'C' (Cytosine) at nucleotide 7.693.225 of chromosome 3, instead of a 'T' (Thymine). The term "SNP genotype" refers to the nucleotide present at the particular SNP. When referring to the "resistance genotype" or "CVYV genotype" or "cyv_3.1 genotype", reference to the nucleotide of the CVYV resistant wild accession is made. Thus, the "resistance genotype" for SNP_02 is 'G' (Guanine) at nucleotide 7.664.093 of chromosome 3 and that of SNP_03 is 'C' (Cytosine) at nucleotide 7.693.225 of chromosome 3. The other (alternative) nucleotide refers to the nucleotide found in the cultivated watermelon lacking the introgression and can be referred to as the WT genotype or susceptible genotype.

The term "SNP haplotype" refers to the nucleotide present at several SNP locations. When referring to the "CVYV haplotype", "resistance haplotype" or "cyv_3.1 haplotype", reference to the SNP genotype of several of the SNP markers linked to cyv_3.1 is made. For example haplotype-A comprises nucleotides G-G-C for SNP_01, SNP_02 and SNP_03, respectively. Haplotype-B comprises nucleotides A-G-C for SNP_01, SNP_02 and SNP_03, respectively.

"Cultivated watermelon genome" and "physical position on the cultivated watermelon genome" and "chromosome 3" refers to the physical genome of cultivated watermelon, world wide web at http://www.icugi.org/cgi-bin/ICuGI/index.cgi under "Watermelon: Genome", "Watermelon genome (97103)—version 1" and the physical chromosomes and the physical position on the chromosomes. So, for example SNP_01 is located at the nucleotide (or 'base') positioned physically at nucleotide 7.586.752 of chromosome 3, SNP_02 is located at the nucleotide (or 'base') positioned physically at nucleotide 7.664.093 of chromosome 3, and SNP_03 is located at the nucleotide (or 'base') positioned physically at nucleotide 7.693.225 of chromosome 3. Chromosome 3 has a physical size from 0 to 28.9 Mb.

"Introgression fragment" or "introgression segment" or "introgression region" refers to a chromosome fragment (or chromosome part or region) which has been introduced into another plant of the same or related species by crossing or traditional breeding techniques, such as backcrossing, i.e. the introgressed fragment is the result of breeding methods referred to by the verb "to introgress" (such as backcrossing). In watermelon, wild watermelon accessions can be used to introgress fragments of the wild genome into the genome of cultivated watermelon genome. Such a cultivated watermelon plant thus has a "genome of cultivated *Citrullus lanatus* ssp. *vulgaris*", but comprises in the genome a fragment of a wild watermelon, e.g. an introgression fragment from *Citrullus lanatus* ssp. *lanatus* or *Citrullus lanatus* ssp. *mucosospermus*. So, for example, a cultivated watermelon is provided herein comprising a genome of cultivated watermelon, and in that genome an introgression fragment from wild watermelon on chromosome 3 which comprises the CVYV-resistance conferring QTL named herein cyv_3.1. It is understood that the term "introgression fragment" never includes a whole chromosome, but only a part of a chromosome. The introgression fragment can be large, e.g. even three quarter or half of a chromosome, but is preferably smaller, such as about 15 Mb or less, such as about 10 Mb or less, about 9 Mb or less, about 8 Mb or less, about 7 Mb or less, about 6 Mb or less, about 5 Mb or less, about 4 Mb or less, about 3 Mb or less, about 2.5 Mb or 2 Mb or less, about 1 Mb (equals 1,000,000 base pairs) or less, or about 0.5 Mb (equals 500,000 base pairs) or less, such as about 200,000 bp (equals 200 kilo base pairs) or less, about 100,000 bp (100 kb) or less, about 50,000 bp (50 kb) or less, about 30,000 bp (30 kb) or less.

A chromosome 3 of cultivated watermelon comprising an introgression fragment which comprises the CVYV-resistance conferring QTL cyv_3.1 is herein also referred to as a "recombinant chromosome 3".

"CVYV resistance" refers to absence of CVYV symptoms on adult leaves (and preferably also in fruits) or statistically significantly less symptoms than susceptible control plants, such as the susceptible variety Sugar Baby. CVYV resistance can, for example, be assessed using a CVYV resistance assay or alternatively in the field or tunnel in growing areas where natural CVYV infection occurs. Various CVYV resistance assays are possible, e.g. as described in the Examples, but in general a CVYV resistance assay may, for example, involve artificial inoculation of the first expanded true leaf of a plurality of seedlings, optionally followed by a second inoculation of the leaf e.g. four or five days later, incubating the seedlings and control plants for a suitable period of time and under suitable conditions and evaluating virus symptoms one or more times post inoculation (e.g. 20 days, 30 days, 40 days, 50 days, 60 days post inoculation). The susceptible control should be severely symptomatic for the test to be successful. Preferably at least 10, 11, 12, 13, 14 or more plants per genotype are included in each replicate and preferably several replicates are carried out. In one aspect, when testing resistance a line or variety is considered resistant if at least 70%, 80%, 90%/0 or 100% of the plants of the line or variety shows no symptoms, while at least 50%, 60%, 70%, 80%/0, 90% or more plants of the susceptible control line or variety shows symptoms.

"Brix" or "degree Brix" or "° brix" refers to the mean total soluble solids content as measured on several mature fruits using a refractometer. Preferably the mean of at least three fruits, each measured between the centre and the rind of the cut-open fruit, is calculated.

"Marketable" in relation to fruit quality means that the watermelon fruits are suitable for being sold for fresh consumption, having good flavour (no off-flavours), a degree brix of at least 9.0, preferably at least 10.0 or at least 11.0 and preferably also a uniform fruit flesh color, being e.g. white (e.g. variety Cream of Saskatchewan), yellow (e.g. variety Yamato Cream 1), orange (e.g. variety Tendersweet), pink (e.g. variety Sadul), pinkish red (e.g. variety Crimson Sweet), red (e.g. variety Sugar Baby) or dark red (e.g. variety Dixie Lee).

"Uniform fruit flesh color" means that the color throughout the mature fruits, when cut open through the middle (midsection), is evenly distributed throughout the fruit flesh, i.e. not patchy. Thus, a red fruit is red throughout the fruit flesh and does not contain white patches. An example of a fruit with uniform red color is the diploid variety Premium F1 (Nunhems).

"Physical distance" between loci (e.g. between molecular markers and/or between phenotypic markers) on the same chromosome is the actually distance expressed in bases or base pairs (bp), kilo bases or kilo base pairs (kb) or megabases or mega base pairs (Mb).

"Genetic distance" between loci (e.g. between molecular markers and/or between phenotypic markers) on the same chromosome is measured by frequency of crossing-over, or recombination frequency (RF) and is indicated in centimorgans (cM). One cM corresponds to a recombination frequency of about 1%.

If no recombinants can be found, the RF is zero and the loci are either extremely close together physically or they are identical. The further apart two loci are, the higher the RF.

"Uniformity" or "uniform" relates to the genetic and phenotypic characteristics of a plant line or variety. Inbred lines are genetically highly uniform as they are produced by several generations of inbreeding. Likewise, and the F1 hybrids and the triploid hybrids which are produced from such inbred lines are highly uniform in their genotypic and phenotypic characteristics and performance.

The term "CVYV-allele" or "CVYV resistance allele" refers to an allele found at the locus cyv_3.1 introgressed into cultivated watermelon (onto cultivated *C. lanatus* ssp. *vulgaris* chromosome 3) from a wild watermelon. The term "CVYV-allele", thus, also encompasses CVYV-alleles obtainable from different wild watermelons. When no dominant susceptible (wild type, WT) allele is present at the locus in the genome (i.e. in diploid watermelon two copies of the CVYV allele are present, in triploid watermelon 3 copies and in tetraploid watermelon 4 copies), the plant line or variety will be CVYV resistant. In cultivated watermelon plants lacking the introgression fragment, the allele found at the same locus on chromosome 3 is herein referred to as "wild type" allele (WT). As the cyv_3.1 is recessive, no wild type allele should be present to express the CVYV-resistance phenotype. Thus, two recombinant chromosomes 3 (in diploid watermelon lines or varieties), three recombinant chromosomes 3 (in triploid watermelon lines or varieties) or four recombinant chromosomes 3 (in tetraploid watermelon lines or varieties) need to be present to express the CVYV-resistance phenotype. The SNP genotypes and SNP haplotypes provided herein are indicative of the presence of the introgression fragment comprising cyv_3.1.

A genetic element, an introgression fragment, or a gene or allele conferring a trait (such as CVYV-resistance) is said to be "obtainable from" or can be "obtained from" or "derivable from" or can be "derived from" or "as present in" or "as found in" a plant or seed or tissue or cell if it can be transferred from the plant or seed in which it is present into another plant or seed in which it is not present (such as into a CVYV-susceptible line or variety) using traditional breeding techniques without resulting in a phenotypic change of the recipient plant apart from the addition of the trait conferred by the genetic element, locus, introgression fragment, gene or allele. The terms are used interchangeably and the genetic element, locus, introgression fragment, gene or allele can thus be transferred into any other genetic background lacking the trait. Not only seeds deposited and comprising the genetic element, locus, introgression fragment, gene or allele can be used, but also progeny/descendants from such seeds which have been selected to retain the genetic element, locus, introgression fragment, gene or allele, can be used and are encompassed herein, such as commercial varieties developed from the deposited seeds or from descendants or ancestors thereof. Likewise, other wild sources containing the genetic element, locus, introgression fragment, gene or allele (e.g. the cyv_3.1 or a variant thereof) can be identified and used to transfer it into cultivated watermelon. Whether a plant (or genomic DNA, cell or tissue of a plant) comprises the same (or variant thereof) genetic element, locus, introgression fragment, gene or allele as obtainable from the deposited seeds can be determined by the skilled person using one or more techniques known in the art, such as phenotypic assays, whole genome sequencing, molecular marker analysis, trait mapping, chromosome painting, allelism tests and the like, or combinations of techniques.

A "Variant" or "orthologous" sequence or a "variant cyv_3.1" refers to a CVYV resistance conferring QTL (cyv_3.1), or an introgression fragment comprising the QTL, which is derived from different wild watermelon plant than the cyv_3.1 present in NCIMB42449 or in NCIMB42450, or in NCIMB42666, but which variant comprises one or more of the resistance genotype of the SNP marker(s), or of the SNP haplotypes, linked to cyv_3.1 and wherein the variant genomic sequence comprises substantial sequence identity to the SEQ ID NO comprising the SNP (any one of SEQ ID NO: 1, SEQ ID NO: 2 or SEQ ID NO: 3), i.e. at least 85%, 90%, 92%, 95%, 98%, 99% sequence identity or more. The SNP in such a variant sequence is then referred to as being "at a nucleotide corresponding to" or "at a nucleotide position corresponding to" the position of the SNP in the original SEQ ID NO. Thus, when the original sequence and the variant sequence are pairwise aligned over the entire length, a SNP at e.g. position 76 in the original sequence will, in the variant, be present at the nucleotide corresponding to nucleotide 76 in the original sequence. Thus, when reference herein is made to a certain SNP resistance genotype in a specific genomic sequence (selected from SEQ ID NO: 1 to SEQ ID NO: 3), this encompasses also the SNP resistance genotype in variants of the genomic sequence, i.e. the SNP resistance genotype in a genomic sequence comprising at least 85%, 90%, 92%, 95%, 98%, 99% sequence identity to the sequence referred to (selected from SEQ ID NO: 1 to SEQ ID NO: 3). Thus, any reference herein to any one of SEQ ID NO: 1 to 3 in one aspect also encompasses a variant of any one of SEQ ID NO: 1 to 3, said variant comprising at least 85%, 90%, 95%, 98%, or 99% sequence identity to said sequence.

The term "marker assay" refers to a molecular marker assay which can be used to test whether on cultivated watermelon chromosome 3 an introgression from a wild watermelon is present which introgression fragment comprises the CVYV-resistance QTL (cyv_3.1 or variant) (or whether a wild watermelon accession comprises the cyv_3.1 or a variant thereof in its genome), by determining the genotype of any one or more markers linked to the cyv_3.1, e.g. the genotype of one or more SNP markers selected from SNP_02 and SNP_03 and (optionally) any wild watermelon genome-specific marker within a distance of 5 Mb, 3 Mb, 2 Mb, 1 Mb, 0.5 Mb, 0.1 Mb, 74 kb, 50 kb, 20 kb, 10 kb, 5 kb, 2 kb, 1 kb or less of SNP_02 or SNP_03. The step of "determining the genotype" may also be referred to as "genotyping". Optionally the marker assay may also include genotyping of SNP_01 and/or SNP_04 and/or any wild watermelon genome-specific marker within a distance of 5 Mb, 3 Mb, 2 Mb, 1 Mb, 0.5 Mb, 0.1 Mb, 74 kb, 50 kb, 20 kb, 10 kb, 5 kb, 2 kb, 1 kb or less of SNP_01 and/or SNP_04.

"Average" or "mean" refers herein to the arithmetic mean and both terms are used interchangeably. The term "average" or "mean" thus refers to the arithmetic mean of several measurements. The skilled person understands that the phenotype of a plant line or variety depends to some extent on growing conditions and that, therefore, arithmetic means of at least 10, 15, 20, 30, 40, 50 or more plants (or plant parts) are measured, preferably in randomized experimental designs with several replicates and suitable control plants (e.g. plants of the variety Sugar Baby, or any other CVYV susceptible variety or line) grown under the same conditions in the same experiment. "Statistically significant" or "statistically significantly" different or "significantly" different refers to a characteristic of a plant line or variety that, when compared to a suitable control show a statistically significant difference in that characteristic (e.g. the p-value is less than 0.05, p<0.05, using ANOVA) from the (mean of the) control.

The term "traditional breeding techniques" encompasses herein crossing, backcrossing, selfing, selection, double haploid production, chromosome doubling, embryo rescue, protoplast fusion, marker assisted selection, mutation breeding etc., all as known to the breeder (i.e. methods other than genetic modification/transformation/transgenic methods), by which, for example, a recombinant chromosome 3 can be obtained, identified and/or transferred.

"Backcrossing" refers to a breeding method by which a (single) trait, such as the CVYV resistance QTL, can be transferred from one (often an inferior) genetic background (e.g. a wild watermelon; also referred to as "donor") into another (often a superior) genetic background (also referred to as "recurrent parent"), e.g. cultivated watermelon. An offspring of a cross (e.g. an F1 plant obtained by crossing e.g. a wild watermelon with a cultivated watermelon, or an F2 plant or F3 plant, etc., obtained from selfing the F1), is "backcrossed" to the parent with e.g. the superior genetic background, e.g. to the cultivated parent. After repeated backcrossing, the trait of the one (often inferior) genetic background will have been incorporated into the other (often superior) genetic background.

"Marker assisted selection" or "MAS" is a process of using the presence of molecular markers (such as SNP markers), which are genetically linked to a particular locus or to a particular chromosome region (e.g. introgression fragment), to select plants for the presence of the specific locus or region (e.g. the introgression fragment). For example, a molecular marker genetically linked to the CVYV resistance QTL, can be used to detect and/or select watermelon plants, or plant parts, comprising the QTL on chromosome 3. The closer the genetic linkage of the molecular marker to the locus, the less likely it is that the marker is dissociated from the locus through meiotic recombination. Likewise, the closer two markers are linked to each other the less likely it is that the two markers will be separated from one another (and the more likely they will co-segregate as a unit).

A molecular marker within 5 Mb, 3 Mb, 2.5 Mb, 2 Mb, 1 Mb, 0.5 Mb, 0.4 Mb, 0.3 Mb, 0.2 Mb, 0.1 Mb, 74 kb, 50 kb, 20 kb, 10 kb, 5 kb, 2 kb, 1 kb or less of another marker, or of a locus, refers to a marker which is physically located within the 5 Mb, 3 Mb, 2.5 Mb, 2 Mb, 1 Mb, 0.5 Mb, 0.4 Mb, 0.3 Mb, 0.2 Mb, 0.1 Mb, 74 kb, 50 kb, 20 kb, 10 kb, 5 kb, 2 kb, 1 kb or less, of the genomic DNA region flanking the marker (i.e. either side of the marker). See e.g. the diagram of FIG. 1, showing a region introgressed from wild watermelon comprising cyv_3.1, whereby markers within 5 Mb of the region enlarged in the diagram are shown.

"LOD-score" (logarithm (base 10) of odds) refers to a statistical test often used for linkage analysis in animal and plant populations. The LOD score compares the likelihood of obtaining the test data if the two loci (molecular marker loci and/or a phenotypic trait locus) are indeed linked, to the likelihood of observing the same data purely by chance. Positive LOD scores favor the presence of linkage and a LOD score greater than 3.0 is considered evidence for linkage. A LOD score of +3 indicates 1000 to 1 odds that the linkage being observed did not occur by chance.

"Transgene" or "chimeric gene" refers to a genetic locus comprising a DNA sequence, such as a recombinant gene, which has been introduced into the genome of a plant by transformation, such as *Agrobacterium* mediated transformation. A plant comprising a transgene stably integrated into its genome is referred to as "transgenic plant".

An "isolated nucleic acid sequence" or "isolated DNA" refers to a nucleic acid sequence which is no longer in the natural environment from which it was isolated, e.g. the nucleic acid sequence in a bacterial host cell or in the plant nuclear or plastid genome. When referring to a "sequence" herein, it is understood that the molecule having such a sequence is referred to, e.g. the nucleic acid molecule.

A "host cell" or a "recombinant host cell" or "transformed cell" are terms referring to a new individual cell (or organism) arising as a result of at least one nucleic acid molecule, having been introduced into said cell. The host cell is preferably a plant cell or a bacterial cell. The host cell may contain the nucleic acid as an extra-chromosomally (episomal) replicating molecule, or comprises the nucleic acid integrated in the nuclear or plastid genome of the host cell, or as introduced chromosome, e.g. minichromosome.

"Sequence identity" and "sequence similarity" can be determined by alignment of two peptide or two nucleotide sequences using global or local alignment algorithms. Sequences may then be referred to as "substantially identical" or "essentially similar" when they are optimally aligned by for example the programs GAP or BESTFIT or the Emboss program "Needle" (using default parameters, see below) share at least a certain minimal percentage of sequence identity (as defined further below). These programs use the Needleman and Wunsch global alignment algorithm to align two sequences over their entire length, maximizing the number of matches and minimising the number of gaps. Generally, the default parameters are used, with a gap creation penalty=10 and gap extension penalty=0.5 (both for nucleotide and protein alignments). For nucleotides the default scoring matrix used is DNAFULL and for proteins the default scoring matrix is Blosum62 (Henikoff & Henikoff, 1992, PNAS 89, 10915-10919). Sequence alignments and scores for percentage sequence identity may for example be determined using computer programs, such as EMBOSS as available on the world wide web under ebi.ac.uk/Tools/psaemboss_needle/). Alternatively sequence similarity or identity may be determined by searching against databases such as FASTA, BLAST, etc., but hits should be retrieved and aligned pairwise to compare sequence identity. Two proteins or two protein domains, or two nucleic acid sequences have "substantial sequence identity" if the percentage sequence identity is at least 85%, 90%, 92%, 95%, 98%, 99% or more (e.g. at least 99.1, 99.2 99.3 99.4, 99.5, 99.6, 99.7, 99.8, 99.9 or more (as determined by Emboss "needle" using default parameters, i.e. gap creation penalty=10, gap extension penalty=0.5, using scoring matrix DNAFULL for nucleic acids an Blosum62 for proteins).

When reference is made to a nucleic acid sequence (e.g. DNA or genomic DNA) having "substantial sequence identity to" a reference sequence or having a sequence identity of at least 80%, e.g. at least 85%, 90%, 92%, 95%, 98%, 99%, 99.2%, 99.5%, 99.9% nucleic acid sequence identity to a reference sequence, in one embodiment said nucleotide sequence is considered substantially identical to the given nucleotide sequence and can be identified using stringent hybridisation conditions. In another embodiment, the nucleic acid sequence comprises one or more mutations compared to the given nucleotide sequence but still can be identified using stringent hybridisation conditions.

"Stringent hybridisation conditions" can be used to identify nucleotide sequences, which are substantially identical to a given nucleotide sequence. Stringent conditions are sequence dependent and will be different in different circumstances. Generally, stringent conditions are selected to be about 5° C. lower than the thermal melting point (Tm) for the specific sequences at a defined ionic strength and pH. The Tm is the temperature (under defined ionic strength and pH) at which 50% of the target sequence hybridises to a perfectly matched probe. Typically stringent conditions will be chosen in which the salt concentration is about 0.02 molar at pH 7 and the temperature is at least 60° C. Lowering the salt concentration and/or increasing the temperature increases stringency. Stringent conditions for RNA-DNA hybridisations (Northern blots using a probe of e.g. 100 nt) are for example those which include at least one wash in 0.2×SSC at 63° C. for 20 min, or equivalent conditions. Stringent conditions for DNA-DNA hybridisation (Southern blots using a probe of e.g. 100 nt) are for example those which include at least one wash (usually 2) in 0.2×SSC at a temperature of at least 50° C., usually about 55° C., for 20 min, or equivalent conditions. See also Sambrook et al. (1989) and Sambrook and Russell (2001).

"Allelism test" refers to a genetic test whereby it can be tested whether a phenotype, e.g. CVYV resistance, seen in two plant lines or varieties are determined by the same gene or locus or by different genes or loci. For example, the plants to be tested are crossed with each other (preferably after selfing to ensure they are homozygous), the segregation of the phenotypes amongst the F1 or further selfing or backcross progeny is determined. The ratio of segregation indicates if the genes or loci are allelic or if they are different. So for example if the alleles are of the same gene, F1 plants (produced by crossing two homozygous plants) will all (100%) have the same phenotype, while that may not be the case if the alleles are of different genes. Likewise in F2 plants phenotypic segregation will indicate whether the same or different genes are involved.

"Fine mapping" refers to methods by which the position of a QTL can be determined more accurately (narrowed down). For example a large population segregating for the trait can be analysed for segregation of the trait (e.g. CVYV resistance) and the DNA markers on chromosome 3 and plants comprising recombination events in the region of chromosome 3 comprising the CVYV resistance locus (see e.g. FIG. 1 striped area) can be selected, in order to determine between which pair of SNP markers the QTL is located. One can also search for additional markers between the most linked pair of marker to narrow down the interval in which the QTL is located.

FIG. 1:

FIG. 1 shows in the left-hand diagram a recombinant chromosome 3 comprising an introgression fragment from wild watermelon (striped region) spanning a 5 Mb region on either side of the SNP markers. The cultivated watermelon regions are not striped (white). On the two enlargements (centre and right-hand diagram) the SNP markers SNP_01 to SNP_04 are shown for a CYCV resistant and ZYMV susceptible plant (center diagram) and for a CVYV resistant and ZYMV resistant plant (right-hand diagram), including the SNP genotypes and locations (chromosome location is indicated in Mb, e.g. 7.5 Mb for SNP_01 and 7.7 Mb for SNP_04): SNP_01 may be either AA or GG depending on the haplotype; SNP_02 has the resistance genotype GG; SNP_03 has the resistance genotype CC; and SNP_04 has either the TT genotype (indicating susceptibility to ZYMV) or the GG genotype (indicating resistance to ZYMV, i.e. presence of a region (hatched region) comprising the zym locus in homozygous form).

DETAILED DESCRIPTION

The inventors found a recessive QTL on chromosome 3 of wild watermelon accessions, which comprises a CVYV resistance conferring locus. They found two different haplotypes linked to the resistance conferring QTL, haplotype A comprised nucleotides G-G-C at SNP_01, SNP_02 and SNP_03, respectively, and haplotype B comprised nucleotides A-G-C at SNP_01, SNP_02 and SNP_03, respectively.

Furthermore, SNP_02 and SNP_03 (the two common SNPs of both resistance haplotypes) were closely linked to the cyv_3.1 locus and were used to backcross the QTL cyv_3.1 into CVYV susceptible cultivated watermelon from two different wild watermelon accessions, thereby introducing CVYV-resistance into cultivated watermelon producing marketable fruits.

Seeds of two diploid inbred lines comprising cyv_3.1 in homozygous form have been deposited by Nunhems B.V. at the NCIMB under accession numbers NCIMB 42449 and NCIMB42450. These two lines comprise SNP_02 and SNP_03 in homozygous form and have SNP haplotype B. The fruits are seeded, red-fleshed fruits having a brix of 11.0 and are marketable fruits. The plants are CVYV resistant and ZYMV susceptible (and also lack the eIF4E marker of Ling et al., 2008 supra). One of the lines has fruits with a Crimson Sweet type rind (NCIMB 42449), the other one (NCIMB42450) has fruits with a Jubilee rind (as in Premium F1). Average fruit weight is 7 kg and 8 kg respectively. In addition, a number of cultivated inbred lines comprising the cyv_3.1 locus have been generated, which have average fruit weights ranging from about 2 kg to about 12 kg.

Seeds of another diploid elite inbred line comprising cyv_3.1 in homozygous form have been deposited by Nunhems B.V. at the NCIMB under accession number NCIMB 42666. This line comprise SNP_02 and SNP_03 in homozygous form and has SNP haplotype A. The fruits are seeded, red-fleshed fruits which are marketable.

least 90%, 91%, 92%, 93%, 94%, 95%, 96%, 97%, 98% or 99% sequence identity to SEQ ID NO: 2; and/or b) a Cytosine (C) at nucleotide 76 of SEQ ID NO: 3 (SNP_03) or at nucleotide 76 of a sequence comprising at least 90%, 91%, 92%, 93%, 94%, 95%, 96%, 97%, 98% or 99% sequence identity to SEQ ID NO: 3; and/or (optionally)

TABLE 1

SNP markers linked to cyv_3.1 and SNP location on chromosome 3 of the cultivated watermelon genome published on the world wide web icugi.org/cgi-bin/ICuGI/index.cgi under "Watermelon: Genome", "Watermelon genome (97103)-version 1"

| SNP marker name | cyv_3.1/cyv_3.1 introgression from *C. lanatus* ssp. *mucosospermus* | cyv_3.1/cyv_3.1 introgression from *C. lanatus* ssp. *lantus* | watermelon variety without cyv_3.1 (WT/WT) | Genomic sequence (5' to 3' direction) comprising the SNP at nucleotide 76 of the sequence, and physical SNP location on cultivated watermelon chromosome 3(*) |
|---|---|---|---|---|
| SNP_01 | GG | AA | GG | GGGGCGAATAAAATAAAATA<br>AATAAATTTGGTAGGGTTGG<br>AGTGGAATAAAGGAGATTTT<br>ATTTTATTTGGTTGA[A/G]*<br>GAAACAAAAAGGGAAAAATT<br>GGAATTAAGGGTTTAAGGAG<br>GGAGAGGAATTAGGGTTTAG<br>TTTAATCCCACCCTC<br>(SEQ ID NO: 1)<br>*Located at nucleotide 7.586.752 |
| SNP_02 | GG | GG | AA | TCAGTCATAGTATAGTGGAA<br>TATTTGACTGCAGGTATAAG<br>ACTCAACTTCAGAAAGATCC<br>AGACCTTTTTTTAA[A/G]*<br>AGAGAGAGAGAGAGAGAGAG<br>AGAGAGAACTAGAAACAACA<br>ATTTCCACCAAAAGAATGAA<br>AAGAGACTAAGACTC<br>(SEQ ID NO: 2)<br>*Located at nucleotide 7.664.093 |
| SNP_03 | CC | CC | TT | CGAGTTGGCTATTAGAGTTG<br>ATCGTTGGAGATGATTGACT<br>GAGTTAGTTGCTAGAGGTGG<br>TCGTTGAGTTGGTTG[C/T]*<br>CGAAGGTATTCGTCAGGGCT<br>AGTTGCGAAGTTGGGCTTTG<br>GAGAAGTGGAGATAGTCATT<br>GTAGTTGATTGATGG<br>(SEQ ID NO: 3)<br>*Located at nucleotide 7.693.225 |
| Phenotype | CVYV resistant | CVYV resistant | CVYV susceptible | |
| SNP haplotype | Resistance Haplotype A: G-G-C for SNP_01, SNP_02 and SNP_03 | Resistance Haplotype B: A-G-C for SNP_01, SNP_02 and SNP_03 | | |

Diploid Cultivated Watermelon Plants, Seeds and Plant Parts Comprising cyv_3.1

In one aspect of the invention (seed of) a diploid cultivated watermelon plant of the species *Citrullus lanatus* ssp. *vulgaris* is provided, wherein said plant comprises an introgression fragment from a wild watermelon plant on chromosome 3, whereby said introgression fragment comprises a CVYV-resistance conferring locus and is optionally detectable by (or comprises) a marker selected from the group consisting of:

a) a Guanine (G) at nucleotide 76 of SEQ ID NO: 2 (SNP_02) or at nucleotide 76 of a sequence comprising at c) a wild watermelon-genome-specific molecular marker within 5 Mb, 3 Mb, 2 Mb, 1 Mb, 0.5 Mb, 0.1 Mb, 74 kb, 50 kb, 20 kb, 10 kb, 5 kb, 2 kb, 1 kb or less of SNP_02 or SNP_03.

The above watermelon plant thus comprises an introgression fragment on chromosome 3 (comprising cyv_3.1), which is detectable by the resistance genotype of SNP_02 and/or SNP_03 and/or optionally another wild-watermelon genome specific marker within 5 Mb of SNP_02 or SNP_03. Although SNP_02 and SNP_03 are closely linked to the QTL, it is possible to generate introgression fragments which have lost SNP_02 and/or SNP_03, but retain the QTL and one or more different wild watermelon-genome-specific markers closely linked to cyv_3.1, as mentioned under c) above. The important contribution to the art is that the introgression fragment comprises the CVYV-resistance locus referred herein to as cyv_3.1. The plant need not be phenotypically CVYV resistant, as the CVYV-resistance locus may be in heterozygous form (only one recombinant chromosome 3 may be present). Thus the diploid genotype for SNP_02 may be either heterozygous GA (Guanine/Adenine) or homozygous GG (Guanine/Guanine) and the diploid genotype for SNP_03 may be either heterozygous CT (Cytosine/Thymine) or homozygous CC (Cytosine/Cytosine). In other words, a plant may be heterozygous for the introgression fragment (and the QTL), having only one Guanine (G) at nucleotide 76 of SEQ ID NO: 2 (SNP_02), or at a nucleotide corresponding to nucleotide 76 of SEQ ID NO: 2 in a variant sequence, i.e. in a sequence comprising at least 90%, 91%, 92%, 93%, 94%, 95%, 96%, 97%, 98% or 99% sequence identity to SEQ ID NO: 2, and only one Cytosine at nucleotide 76 of SEQ ID NO: 3 (SNP_03), or at a nucleotide corresponding to nucleotide 76 of SEQ ID NO: 3 in a variant sequence, i.e. in a sequence comprising at least 90%, 91%, 92%, 93%, 94%, 95%, 96%, 97%, 98% or 99% sequence identity to SEQ ID NO: 3; or it may be homozygous for the introgression fragment (and the QTL) having two Guanines at nucleotide 76 of SEQ ID NO: 2 (SNP_02) or at a nucleotide corresponding to nucleotide 76 of SEQ ID NO: 2 in a variant sequence, i.e. in a sequence of a sequence comprising at least 90%, 91%, 92%, 93%, 94%, 95%, 96%, 97%, 98% or 99% sequence identity to SEQ ID NO: 2 and having two Cytosine (C) at nucleotide 76 of SEQ ID NO: 3 (SNP_03) or at a nucleotide corresponding to nucleotide 76 of SEQ ID NO: 3 in a variant sequence, i.e. in a sequence comprising at least 90%, 91%, 92%, 93%, 94%, 95%, 96%, 97%, 98% or 99% sequence identity to SEQ ID NO: 3. The same applies to the wild watermelon-genome-specific markers, linked to cyv_3.1, under c) above, i.e. this marker may be heterozygous or homozygous. The markers under c) can be identified by e.g. sequencing the region. These markers may be any markers which are linked to cyv_3.1 and which are polymorphic between the wild watermelon genomic DNA and the cultivated watermelon genomic DNA, such as SNP markers, insertions or deletions of one or more nucleotides (e.g. INDEL markers), AFLP markers, etc.

In one aspect the introgression fragment is in homozygous form, and the introgression fragment comprising the CVYV locus cyv_3.1 is in homozygous form, whereby the plant is CVYV resistant, as e.g. determinable in a CVYV resistance assay and/or a molecular marker assay. Thus in one aspect the SNP_02, SNP_03 and/or the wild watermelon-genome-specific marker are homozygous, i.e. SNP_02 and SNP_03 have the resistance genotype GG and CC, respectively, and the plant is CVYV resistant, e.g. when tested in a CVYV resistance assay and preferably also when grown in the field or tunnel under natural CVYV pressure.

As mentioned the wild watermelon-genome-specific markers may be any type of molecular marker present on the introgression fragment comprising cyv_3.1 and distinguishing the introgression fragment from the cultivated watermelon chromosome 3 region (WT genotype, lacking cyv_3.1), e.g. one or more SNP markers, CAPS markers, RFLP markers, AFLP markers, microsatellite markers, minisatellite markers, insertions or deletions of one or more nucleotides (e.g. INDELs), etc. Thus a "wild watermelon-genome-specific molecular marker" is a marker which is polymorphic or distinct between the wild watermelon genome introgression fragment comprising cyv_3.1 and the cultivated watermelon genome lacking the introgression fragment. Polymorphic SNP markers have already been provided herein, but other markers can be easily developed by the skilled person, e.g. by mapping or fine mapping or sequencing the region on chromosome 3 comprising the introgression fragment. For example the chromosome 3 region of plants deposited, comprising the introgression fragment in homozygous form, can be sequenced and compared to the same region of cultivated watermelon chromosome 3 in order to identify other wild watermelon-genome-specific molecular markers within 5 Mb, 3 Mb, 2 Mb, 1 Mb, 0.5 Mb, 0.1 Mb, 74 kb, 50 kb, 20 kb, 10 kb, 2 kb, 1 kb or less of SNP_02 or of SNP_03, i.e. other wild watermelon-genome-specific markers linked to SNP_2 and/or SNP_03 and thus indicative of the introgression fragment comprising cyv_3.1.

Thus in one aspect said introgression fragment is detectable by (or comprises) a marker selected from the group consisting of:
a) a diploid genotype GG (Guanine/Guanine) at nucleotide 76 of SEQ ID NO: 2 (SNP_02) or of a sequence comprising at least 90%, 91%, 92%/0, 93%, 94%, 95%, 96%, 97%, 98% or 99% sequence identity to SEQ ID NO: 2; and/or
b) a diploid genotype CC (Cytosine/Cytosine) at nucleotide 76 of SEQ ID NO: 3 (SNP_03) or of a sequence comprising at least 90%, 91%, 920/0, 93%, 94%, 95%, 96%, 97%, 98% or 99% sequence identity to SEQ ID NO: 3; and/or
c) a wild watermelon-genome-specific molecular marker within 5 Mb, 3 Mb, 2 Mb, 1 Mb, 0.5 Mb, 0.1 Mb, 74 kb, 50 kb, 20 kb, 10 kb, 5 kb, 2 kb, 1 kb or less of SNP_02 or SNP_03 which marker is in homozygous form.

When referring herein to a SNP genotype at a specific position, e.g. at nucleotide 76 of SEQ ID NO: 2, "or of a sequence comprising at least 90%/0, 91%, 92%, 93%, 94%, 95%, 96%, 97%, 98% or 99% sequence identity to the SEQ ID NO", this means that the SNP genotype is present in a variant sequence at a nucleotide corresponding to the same nucleotide (e.g. corresponding to nucleotide 76 of SEQ ID NO: 2) in the variant sequence, i.e. in a sequence comprising at least 90%, 91%, 92%, 93%, 94%, 95%, 96%, 97%, 98% or 99%/0 sequence identity to the mentioned SEQ ID NO. It may for example be that the variant sequence is one or a few nucleotides shorter, but when one pairwise aligns the variant sequence with the mentioned SEQ ID NO, one can see which nucleotide of the variant sequence corresponds to the same nucleotide. In the variant sequence this may for example be nucleotide number 75 or 77 of that variant sequence which corresponds to nucleotide 76 of the mentioned sequence.

The above plant is, thus, also CVYV resistant in its phenotype, as determinable in a CVYV resistance assay as e.g. described in the Examples, or in the field or tunnel in areas where CVYV occurs naturally. It is understood that in a CVYV resistance assay a plurality of plants (e.g. at least 10, 11, 12, 13, 14, or more) of the line or variety are tested, preferably in several replicates (e.g. 2, 3, 4 or more), and optionally in several locations, and by including a plurality of plants of a susceptible control variety in the same assay. Seeds of the deposited lines can be included as a positive control. All current watermelon varieties are CVYV susceptible, so that any variety or parent line of any such variety can be used as susceptible control, for example the old diploid variety Sugar Baby may be used or Dumara (Nunhems) may be used.

In a specific embodiment of the invention (seed of) a diploid cultivated watermelon plant of the species *Citrullus*

*lanatus* ssp. *vulgaris* is provided, wherein said plant comprises an introgression fragment from a wild watermelon plant on chromosome 3, whereby said introgression fragment comprises a CVYV-resistance conferring locus and is detectable by (or comprises):
a) a Guanine (G) at nucleotide 76 of SEQ ID NO: 2 (SNP_02) or of a sequence comprising at least 90%, 91%, 92%, 93%, 94%, 95%, 96%, 97%, 98% or 99% sequence identity to SEQ ID NO: 2; and/or
b) a Cytosine (C) at nucleotide 76 of SEQ ID NO: 3 (SNP_03) or of a sequence comprising at least 90%/0, 91%, 92%, 93%, 94%, 95%, 96%, 97%, 98% or 99% sequence identity to SEQ ID NO: 3.

The plant comprises the CVYV resistance locus in homozygous or heterozygous form.

In one aspect the plant comprises the introgression fragment in homozygous form, i.e. the introgression fragment is detectable by (or comprises):
a) a diploid genotype GG (Guanine/Guanine) for nucleotide 76 of SEQ ID NO: 2 (SNP_02) or of a sequence comprising at least 90%/0, 91%, 92%/0, 93%, 94%, 95%, 96%, 97%, 98% or 99% sequence identity to SEQ ID NO: 2; and/or
b) a diploid genotype CC (Cytosine/Cytosine) at nucleotide 76 of SEQ ID NO: 3 (SNP_03) or of a sequence comprising at least 90%/0, 91%, 920/0, 93%, 94%, 95%, 96%, 97%, 98% or 99% sequence identity to SEQ ID NO: 3.

The above diploid plants may in one embodiment have SNP haplotype A or SNP-haplotype B. Thus, in one aspect the plants comprise SNP haplotype A having G-G-C for SNP_01-SNP_02 and SNP_03, respectively (e.g. in diploid form the SNP haplotype A is either GG-GG-CC in homozygous form, or GG-GA-CT in heterozygous form). In another aspect the plant comprises SNP haplotype B having A-G-C for SNP_01-SNP_02 and SNP_03, respectively (e.g. in diploid form the SNP haplotype A is either AA-GG-CC in homozygous form, or AG-GA-CT in heterozygous form). Thus, at nucleotide 76 of SEQ ID NO: 1 (SNP_01) or of a sequence comprising at least 90%/0, 91%, 92%, 93%, 94%, 95%, 96%, 97%, 98% or 99% sequence identity to SEQ ID NO:1, the SNP genotype may be either a Guanine or an Adenine. SNP_01 can distinguish the two different resistance haplotypes.

Any of the above described diploid watermelon plants may be of any type, i.e. the cyv_3.1 resistance locus may be introduced into any cultivated watermelon to produce lines or varieties comprising the CVYV locus. Cultivated watermelons produce diverse fruit sizes (e.g. very small, as described in WO2012069539, e.g. less than 0.9 kg or even equal to or less than 0.65 kg; personal-size of about 3-7 pounds, i.e. about 1.4 to 3.2 kg; icebox sizes of about 6-12 pounds, i.e. about 2.7 to 5.5 kg; and larger sizes of up to 35 pounds, i.e. about 15.9 kg), fruit flesh colors, and fruit shapes and with different rind colors. The cyv_3.1 locus may, therefore, be introduced into cultivated watermelon producing any fruit shape (e.g. elongate, oval, oval elongated, blocky, blocky elongated, spherical or round), fruit surface (e.g. furrow, smooth), flesh color (e.g. red, dark red, scarlet red, coral red, orange, salmon or pink, yellow, canary yellow or white), rind color (e.g. light green; dark green; green-striped with narrow, medium or wide stripes; grey types; with or without spotting; Golden yellow; Crimson type rind, Jubilee type rind; Allsweet type rind; black/dark green), rind thickness, rind toughness, rind pattern (e.g. striped, non-striped, netted), flesh structure/flesh firmness, lycopene and/or vitamin content, different sugar to acid ratios, very good fruit flavour, etc. by breeding. See Guner and Wehner 2004, Hort Science 39(6): 1175-1182, in particular pages 1180-1181 describing genes for fruit characteristics. Generally important breeding objectives are early maturity, high fruit yield, high internal fruit quality (good uniform color, high sugar, proper sugar:acid ratio, good flavour, high vitamin and lycopene content, firm flesh texture, non-fibrous flesh texture, freedom from defects such as hollow heart, rind necrosis, blossom-end rot or cross stitch and good rind characteristics and cracking-resistance).

The fruits produced by the diploid line or variety are preferably marketable fruits.

In one aspect the average brix is at least 6.0, 7.0, 8.0 or at least 9.0, preferably at least 10.0, more preferably at least 11.0 or more.

Fruit color may be any color, such as red, dark red, scarlet red, coral red, orange, salmon, pink, pinkish red, yellow, canary yellow or white. Preferably the fruit flesh color is uniform.

The diploid may be an inbred line or a diploid hybrid, produced by crossing two inbred lines. In one aspect both inbred parent lines are homozygous for the cyv_3.1, so that the hybrid is also homozygous.

The diploid plant may be an inbred line, a variety, a diploid F1 hybrid, an OP (open pollinated) variety, a pollenizer plant, (e.g. a dedicated pollenizer producing marketable fruits as described in WO2012069539), or any other cultivated diploid, including any clonally propagated plant. As the CVYV resistance phenotype is preferably phenotypically expressed, the introgression fragment is in one aspect homozygous in the diploid, as are the one or more of the markers linked to cyv_3.1.

The wild watermelon introgression fragment comprising cyv_3.1 may be of various sizes, e.g. about 15 Mb or less, about 10 Mb or less, about 9 Mb or less, about 8 Mb or less, about 7 Mb or less, about 6 Mb or less, about 5 Mb or less, about 4 Mb or less, about 3 Mb or less, about 2.5 Mb or 2 Mb or less, about 1 Mb (equals 1,000,000 base pairs) or less, or about 0.5 Mb (equals 500,000 base pairs) or less, such as about 200,000 bp (equals 200 kilo base pairs) or less, about 100,000 bp (100 kb) or less, about 50,000 bp (50 kb) or less, about 30,000 bp (30 kb) or less. Smaller introgression fragments are generally preferred, as negative traits may be located on the same fragment. Size of an introgression fragment can be reduced by meiotic recombination (e.g. by selfing the plant) and selecting recombinant progeny plants having a smaller introgression fragment but retaining cyv_3.1, using e.g. a phenotypic assay and/or a molecular marker assay as described herein. If SNP_01 and/or SNP_02 and/or SNP_03 are lost through recombination, but the plant retains the cyv_3.1 locus, phenotypic selection can be used to select a plant retaining cyv_3.1 and/or the introgression fragment can be detected using another method, e.g. sequencing the region of chromosome 3 where the QTL is found (e.g. the region between about 2.50 Mb and about 12.8 Mb of chromosome 3, see FIG. 1) or other wild watermelon-genome-specific markers linked to cyv_3.1. Such other wild watermelon genome specific markers can be developed using methods known to the skilled person, such as fine mapping, sequencing, etc.

In one aspect the introgression fragment of the invention (comprising cyv_3.1 or a variant thereof and wherein the introgression fragment is introgressed from a wild watermelon plant) is a fragment comprising (or spanning) the region starting at 2.50 Mb and ending at 12.80 Mb of chromosome 3 and comprises the cyv_3.1 locus or a variant thereof.

In another aspect the introgression fragment of the invention (comprising cyv_3.1 or a variant thereof and wherein the introgression fragment is introgressed from a wild watermelon plant) is a fragment comprising a smaller fragment (part) of the region starting at 2.50 Mb and ending at 12.80 Mb of chromosome 3, e.g. having a size of e.g. 9 Mb, 8 Mb, 7 Mb, 6 Mb, 5 Mb, 4 Mb, 3 Mb, 2 Mb, 1 Mb, 0.5 Mb, 100 kb, 50 kb, 35 kb, 30 kb, 20 kb, or less (as described above) and comprising the cyv_3.1 locus or a variant thereof. In one aspect the part is at least 5 kb, 10 kb, 20 kb in size, or more.

In yet another aspect the introgression fragment of the invention (comprising cyv_3.1 or a variant thereof and wherein the introgression fragment is introgressed from a wild watermelon plant) consist of a smaller fragment (sub-fragment) of the region starting at 2.50 Mb and ending at 12.80 Mb of chromosome 3, e.g. having a size of e.g. 9 Mb, 8 Mb, 7 Mb, 6 Mb, 5 Mb, 4 Mb, 3 Mb, 2 Mb, 1 Mb, 0.5 Mb, 100 kb, 50 kb, 35 kb, 30 kb, 20 kb, or less (as described above) and comprising the cyv_3.1 locus or a variant thereof. In one aspect the part is at least 5 kb, 10 kb, 20 kb in size, or more.

In yet a further aspect the introgression fragment of the invention (comprising cyv_3.1 or a variant thereof and wherein the introgression fragment is introgressed from a wild watermelon plant) comprises the region starting at starting at 7.50 Mb and ending at 7.75 Mb chromosome 3, or the region starting at 7.60 Mb and ending at 7.70 Mb, wherein the fragment comprises the cyv_3.1 locus or a variant thereof. In one aspect the part is at least 5 kb, 10 kb, 20 kb in size, or more.

Also seeds from which the plants of the invention can be grown are provided herein.

Likewise plant parts of the plants of the invention are encompassed herein, such as cells, roots, leaves, fruits, fruit parts, pollen, ovules, flowers, rootstocks, scions, cuttings, stems, DNA extracted from such parts or cells, etc. Such plant parts comprise in their genome at least one recombinant chromosome 3 comprising the introgression fragment, detectable by one or more markers as described. Likewise genomic DNA extracted from such cells or plant parts comprises in its genome at least one recombinant chromosome 3 comprising the introgression fragment, detectable by one or more markers as described.

The *C. lanatus* ssp. *mucosospermus* CVYV resistance source was a wild accession obtained from the US GRIN collection. It has small (about 13 cm×13 cm) white-fleshed fruits with a brix of about 3.0. The *C. lanatus* ssp. *lanatus* accession was also a wild accession obtained from the US GRIN collection. It had yellow bitter fruits of about 16 cm×24 cm, with a brix below 3.0.

The resistance cyv_3.1 was backcrossed from these two diploid wild accessions into CVYV susceptible watermelon elite lines, thereby generating diploid cultivated watermelon comprising cyv_3.1 and being resistant against CVYV, when the introgression fragment was present in homozygous form.

As mentioned above, seeds of two diploid inbred cultivated watermelon lines comprising cyv_3.1 in homozygous form have been deposited at the NCIMB under accession numbers NCIMB42449 and NCIMB42450. These two lines comprise SNP_02 and SNP_03 in homozygous form and have SNP haplotype B. The fruits are seeded, red-fleshed fruits having a brix of 11.0 and are thus marketable fruits. The plants are CVYV resistant but ZYMV susceptible (and also lack the eIF4E marker of Ling et al. 2008 supra). One of the lines has fruits with a Crimson sweet rind, the other one has fruits with a Jubilee rind. The cyv_3.1 can be transferred from these two lines into any other cultivated watermelon line or variety by traditional breeding, using either phenotypic selection or marker selection or both.

Also seeds of another diploid elite inbred line comprising cyv_3.1 in homozygous form have been deposited by Nunhems B.V. at the NCIMB under accession number NCIMB 42666. This line comprise SNP_02 and SNP_03 in homozygous form and has SNP haplotype A. The fruits are seeded, red-fleshed fruits which are marketable. The plants are CVYV resistant.

In one aspect the cyv_3.1 is obtainable from (can be obtained from/is as present in) seeds deposited under NCIMB42449 or NCIMB 42450 or NCIMB 42666, e.g. by crossing plants grown from such seeds (or progeny thereof) with another watermelon plant and selecting progeny comprising the introgression fragment. In one aspect the other watermelon plant is a cultivated watermelon which is lacks cyv_3.1.

Alternatively other wild accessions of *C. lanatus* ssp. *mucosospermus* or of *C. lanatus* ssp. *lanatus* may comprise cyv_3.1 (or a variant thereof) and may be used to introgress cyv_3.1 (or a variant thereof) into cultivated watermelon. To identify such other wild accessions one or more of the markers provided herein can be used, optionally in combination with CVYV resistance assays. For example, the seeds of the wild watermelon accession PI1189318, was found to comprise cyv_3.1, as shown in Example 6, when screening progeny of wild watermelon accessions of the US GRIN collection using the SNP markers provided herein. PI189318 produce hard white fleshed fruits, which are bitter and which have a very low brix (about 3.0). The cyv_3.1 locus can be introgressed from this, or other wild watermelon accessions, into cultivated watermelon as described herein, optionally using one or more of the SNP markers provided herein. Thus in one aspect the cultivated watermelon plant of the invention comprises an introgression fragment from e.g. PI1189318 or progeny thereof, or from other wild watermelons, whereby the introgression fragment comprises the cvy_3.1 resistance locus and is detectable by one or more markers linked to cvy_3.1 as described herein. The wild watermelons may be of SNP haplotype A or B. For example PI189318 has SNP haplotype A in homozygous form.

In one embodiment of the invention (seed of) a diploid cultivated watermelon plant of the species *Citrullus lanatus* ssp. *vulgaris* is provided, wherein said plant comprises an introgression fragment from a wild watermelon plant on chromosome 3, whereby said introgression fragment comprises a CVYV-resistance conferring locus, whereby said introgression fragment comprises:

a) a Guanine (G) at nucleotide 7.664.093 of the cultivated watermelon genome chromosome 3 (SNP_02); and/or b) a Cytosine (C) at nucleotide 7.693.225 of the cultivated watermelon genome chromosome 3 (SNP_03); and/or optionally c) a wild watermelon-genome-specific molecular marker within 5 Mb, 3 Mb, 2 Mb, 1 Mb, 0.5 Mb, 0.1 Mb, 74 kb, 50 kb, 20 kb, 10 kb, 5 kb, 2 kb, 1 kb or less of SNP_02 or SNP_03.

In another embodiment of the invention (seed of) a diploid cultivated watermelon plant of the species *Citrullus lanatus* ssp. *vulgaris* is provided, wherein said plant comprises an introgression fragment from a wild watermelon plant on chromosome 3, whereby said introgression fragment comprises a CVYV-resistance conferring locus and whereby said introgression fragment is detectable by (or comprises) a marker selected from the group consisting of:

a) a Guanine (G) at nucleotide 76 of SEQ ID NO: 2 (SNP_02) or of a nucleic acid molecule which hybridizes under stringent conditions to SEQ ID NO: 2; and/or b) a Cytosine (C) at nucleotide 76 of SEQ ID NO: 3 (SNP_03) or of a nucleic acid molecule which hybridizes under stringent conditions to SEQ ID NO: 3; and/or optionally c) a wild watermelon-genome-specific molecular marker within 5 Mb, 3 Mb, 2 Mb, 1 Mb, 0.5 Mb, 0.1 Mb, 74 kb, 50 kb, 20 kb, 10 kb, 5 kb, 2 kb, 1 kb or less of SNP_02 or SNP_03.

In a different embodiment of the invention (seed of) a diploid cultivated watermelon plant of the species *Citrullus lanatus* ssp. *vulgaris* is provided, wherein said plant comprises an introgression fragment from a wild watermelon plant on chromosome 3, whereby said introgression fragment comprises a CVYV-resistance conferring locus and whereby said introgression fragment is detectable by (or comprises) a marker selected from the group consisting of:

a) a Guanine (G) at nucleotide 76 of SEQ ID NO: 2 (SNP_02) or of a sequence comprising at least 90%, 91%, 92%, 93%, 94%, 95%, 96%, 97%, 98% or 99% sequence identity to SEQ ID NO: 2; and/or b) a Cytosine (C) at nucleotide 76 of SEQ ID NO: 3 (SNP_03) or of a sequence comprising at least 90%, 91%, 92%, 93%, 94%, 95%, 96%, 97%, 98% or 99% sequence identity to SEQ ID NO: 3; and/or optionally c) a wild watermelon-genome-specific molecular marker within 5 Mb, 3 Mb, 2 Mb, 1 Mb, 0.5 Mb, 0.1 Mb, 74 kb, 50 kb, 20 kb, 10 kb, 5 kb, 2 kb, 1 kb or less of SNP_02 or SNP_03.

In one aspect the introgression fragment, and the markers, are homozygous.

In one aspect, the plants of the invention lack a ZYMV resistance conferring locus on chromosome 3. However, CVYV resistance can also be combined with ZYMV resistance on chromosome 3 as described below.

Also plant parts, such as fruits or parts thereof, cells, leaves, flowers, etc. of the above plants are encompassed herein. As mentioned previously, fruits are marketable diploid fruits.

In one embodiment the cultivated watermelon plant or plant part comprising the CVYV-resistance conferring locus as found in seeds deposited under accession numbers NCIMB 42449 or NCIMB 42450 or NCIMB 42666 or as found in wild watermelon PI189318 or other wild watermelons. Thus in one aspect cyv_3.1 is obtainable by (can be obtained by) crossing a watermelon plant of which seeds were deposited under Accession number NCIMB42449 or NCIMB42450 or NCIMB42666, or progeny of any of these plants (e.g. obtained by selfing and/or crossing and which progeny retain the cyv_3.1), with another watermelon plant, e.g. a cultivated watermelon elite line or variety. In another aspect the cyv_3.1 gene is obtainable by introgressing the resistance from wild watermelons, such as PI189318 or other wild watermelons, into cultivated watermelon.

In another aspect the cultivated watermelon plant or plant part comprising the CVYV-resistance conferring introgression fragment as found in seeds deposited under accession numbers NCIMB 42449 or NCIMB 42450 or NCIMB 42666, or a shorter part thereof, which retains cyv_3.1. Thus in one aspect the introgression fragment comprising cyv_3.1 is obtainable by (can be obtained by) crossing a watermelon plant of which seeds were deposited under Accession number NCIMB42449 or NCIMB42450 or NCIMB42666, or progeny of any of these plants (e.g. obtained by selfing and/or crossing and which progeny retain the cyv_3.1), with another watermelon plant.

Thus, the CVYV resistance gene on chromosome 3 is in one aspect the gene as present in seeds deposited under Accession Number NCIMB42449 or NCIMB42450 or NCIMB42666, or progeny thereof, but it may equally be the resistance gene of another wild watermelon, especially a wild watermelon comprising one or more of the SNP markers, i.e. the resistance genotype of the SNP markers, linked to cyv_3.1. Examples are wild accessions such as PI189318 or others. In addition to marker analysis or as an alternative e.g. an allelism test can easily be carried out by the skilled person in order to determine whether such a CVYV resistance is indeed conferred by the same resistance gene, namely cyv_3.1. Likewise other methods or combinations of methods can be used, such as mapping, fine mapping, sequencing, genetic inheritance, and the like to confirm that the same gene, cyv_3.1, is responsible for the CVYV resistance phenotype.

Combining cyv_3.1 Conferring CVYV Resistance with ZYMV Resistance

The inventors found that cyv_3.1 is located on the same chromosome as the recessive zym gene, which confers resistance against ZYMV. Therefore cyv_3.1 can be combined with zym on chromosome 3 to provide a chromosome that comprises CVYV and ZYMV resistance-conferring loci in coupling phase.

ZYMV is a virus transmitted by aphids and can cause slight to severe fruit deformation and discoloration.

Sources for zym resistance are for example PI595203 as described by Ling et al. 2008 (supra). The inventors have converted the CAPS marker described by Ling et al. 2008 into a SNP marker referred to as SNP_04, see Table 2.

TABLE 2

SNP marker in the eIF4E gene linked to ZYMV resistance and SNP location on chromosome 3 of the cultivated watermelon genome published on the world wide web icugi.org/cgi-bin/ICuGI/index.cgi under "Watermelon: Genome", "Watermelon genome (97103)-version 1"

| SNP marker name | Watermelon with zym/zym introgression from e.g. PI595203 | Watermelon variety without zym/zym | Genomic sequence (5′ to 3′ direction) comprising the SNP at nucleotide 70 of the sequence, and physical SNP location on cultivated watermelon chromosome 3 (*) |
|---|---|---|---|
| SNP_04 | GG | TT | TGAAGTTCTACCTCCAAAAC TCCTCAACAGTAGAGAAGGT ATAGATCGGTCGGATAGACG CACCCCAGG[G/T]*GGCTT GCTTAGACTTGGCGGATGGG TTATCGAACCAAAAGGTCCA |

TABLE 2-continued

SNP marker in the eIF4E gene linked to ZYMV resistance and SNP location on chromosome 3 of the cultivated watermelon genome published on the world wide web icugi.org/cgi-bin/ICuGI/index.cgi under "Watermelon: Genome", "Watermelon genome (97103)-version 1"

| SNP marker name | Watermelon with zym/zym introgression from e.g. PI595203 | Watermelon variety without zym/zym | Genomic sequence (5' to 3' direction) comprising the SNP at nucleotide 70 of the sequence, and physical SNP location on cultivated watermelon chromosome 3 (*) |
|---|---|---|---|
| | | | AGAGTGCTCAAGAGGGTGAG GCTGATGCACTATCGCCGCC GACAAATTGGACGAGTCAAG GTCGTCGTCTCCGACGATCT CTCCTTCCTCAAGTTCCTCA TCTTCATCACCGCCTCGTCC TCTAGGGTTTTGATTTGCAA TGGTATTAGAAAGATCTTCC GTGGATGTAGCTTTGATCGT CTCTTCGACTACCATTTTCC TTTCACTACTTGTGGAATTG AGCGT (SEQ ID NO: 4) *Located at nucleotide 7.767.975 |
| Phenotype | ZYMV resistant | ZYMV susceptible | |

The diploid watermelon plants of the invention described above may, thus, further comprise the zym gene on chromosome 3.

Thus, in one aspect a of the invention (seed of) a diploid cultivated watermelon plant of the species *Citrullus lanatus* ssp. *vulgaris* is provided, wherein said plant comprises an introgression fragment from a wild watermelon plant on chromosome 3 comprising a CVYV resistance conferring locus, whereby said introgression fragment is detectable by (or comprises) a marker selected from the group consisting of:
a) a Guanine (G) at nucleotide 76 of SEQ ID NO: 2 (SNP_02) or of a sequence comprising at least 90%, 91%, 92%, 93%, 94%, 95%, 96%, 97%, 98% or 99% sequence identity to SEQ ID NO: 2; and/or
b) a Cytosine (C) at nucleotide 76 of SEQ ID NO: 3 (SNP_03) or of a sequence comprising at least 90%, 91%, 92%, 93%, 94%, 95%, 96%, 97%, 98% or 99% sequence identity to SEQ ID NO: 3; and/or
c) a wild watermelon-genome-specific molecular marker within 5 Mb, 3 Mb, 2 Mb, 1 Mb, 0.5 Mb, 0.1 Mb, 74 kb, 50 kb, 20 kb, 10 kb, 5 kb, 2 kb, 1 kb or less of SNP_02 or SNP_03; and
d) wherein the plant further comprises the zym gene on chromosome 3.

Optionally, the presence of (an introgression fragment comprising) the zym gene is by detecting a Guanine (G) at nucleotide 70 of SEQ ID NO: 4 (SNP_04) or of a sequence comprising at least 90%/0, 91%, 92%, 93%, 94%, 95%, 96%, 97%, 98% or 99% sequence identity to SEQ ID NO: 4. However, SNP_04 is probably not very closely linked to zym, so that phenotypic selection or the development of a more closely linked marker may be preferred to ensure that zym is present.

The recombinant chromosome 3, thus, comprises the introgression fragment comprises the CVYV resistance locus cyv_3.1 and may further comprise (an introgression fragment comprising) the zym gene on the same chromosome. The plant need not be phenotypically CVYV resistant and ZYMV resistant, as the CVYV resistance locus and the zym gene may be in heterozygous form (only one recombinant chromosome 3 may be present). In one aspect, the plant is homozygous for the recombinant chromosome 3 and thus resistant against both CVYV and ZYMV.

Thus, in one aspect the introgression fragment comprising the CVYV resistance locus cyv_3.1 is in homozygous form, and the (introgression fragment comprising) zym gene is in homozygous form, whereby the plant is CVYV and ZYMV resistant. In one aspect the SNP_02 and/or SNP_03 and/or the wild watermelon genome specific marker(s) linked to cyv_3.1 are homozygous and zym is homozygous (zym/zym), and optionally SNP_04 (if present) is homozygous GG (Guanine/Guanine).

In a specific embodiment of the invention (seed of) a diploid cultivated watermelon plant of the species *Citrullus lanatus* ssp. *vulgaris* is provided, wherein said plant comprises an introgression fragment from a wild watermelon plant on chromosome 3 comprising a CVYV resistance conferring locus named cyv_3.1, whereby said introgression fragment is detectable by (or comprises):
a) a Guanine (G) at nucleotide 76 of SEQ ID NO: 2 (SNP_02) or of a sequence comprising at least 90%, 91%, 92%/0, 93%, 94%, 95%, 96%, 97%, 98% or 99% sequence identity to SEQ ID NO: 2; and
b) a Cytosine (C) at nucleotide 76 of SEQ ID NO: 3 (SNP_03) or of a sequence comprising at least 90%/0, 91%, 92%, 93%, 94%, 95%, 96%, 97%, 98% or 99%/0 sequence identity to SEQ ID NO: 3; and
c) wherein the chromosome 3 further comprises the zym gene.

In one aspect the plant comprises the introgression fragment on chromosome 3 in homozygous form, i.e. the introgression fragment is detectable by (or comprises):
a) a diploid genotype GG (Guanine/Guanine) for nucleotide 76 of SEQ ID NO: 2 (SNP_02) or of a sequence comprising at least 90%/0, 91%, 920/0, 93%, 94%, 95%, 96%, 97%, 98% or 99% sequence identity to SEQ ID NO: 2; and
b) a diploid genotype CC (Cytosine/Cytosine) at nucleotide 76 of SEQ ID NO: 3 (SNP_03) or of a sequence comprising at least 90%, 91%, 92%, 93%, 94%, 95%, 96%, 97%, 98% or 99% sequence identity to SEQ ID NO: 3; and c) wherein the chromosome 3 further comprises the zym gene in homozygous form (zym/zym); and d) wherein the plant is CVYV and ZYMV resistant.

The above diploid plants may in one embodiment have CVYV SNP haplotype A or SNP-haplotype B combined with the zym gene. Thus, in one aspect the plants comprise SNP haplotype A having G-G-C for SNP_01 and SNP_02 and SNP_03, respectively (e.g. in diploid form the SNP haplotype A is either GG-GG-CC in homozygous form or GG-GA-CT in heterozygous form) and the zym gene linked on the same chromosome as cyv_3.1 (and optionally SNP_04 has the diploid genotype GT, heterozygous, or GG, homozygous). In another aspect the plant comprises SNP haplotype B having A-G-C for SNP_01 and SNP_02 and SNP_03, respectively (e.g. in diploid form the SNP haplotype A is either AA-GG-CC in homozygous form or AG-GA-CT in heterozygous form) and the zym gene linked on the same chromosome as cyv_3.1 (and optionally SNP_04 has the diploid genotype GT, heterozygous, or GG, homozygous). Thus, at nucleotide 76 of SEQ ID NO: 1 (SNP_01) or of a sequence comprising at least 90%, 91%, 92%, 93%, 94%, 95%, 96%, 97%, 98% or 99% sequence identity to SEQ ID NO:1, the SNP genotype may be either a Guanine or an Adenine. SNP_01 can distinguish the two different CVYV resistance haplotypes, but either haplotype may be combined with the zym gene on the same chromosome 3.

A diploid CVYV and ZYMV resistant plant may, thus, comprise one of the following two genotypes:

| SNP marker and gene on chromosome 3 | Diploid SNP genotype | Diploid SNP genotype |
|---|---|---|
| SNP_01 | GG | AA |
| SNP_02 | GG | GG |
| SNP_03 | CC | CC |
| gene | zym/zym | zym/zym |
| Optionally SNP_04 | GG | GG |

To combine the CVYV resistance locus cyv_3.1 with the zym gene, the skilled person will cross a plant of the invention, comprising cyv_3.1, with a plant comprising the zym gene and select a recombinant progeny plant comprising both the CVYV locus cyv_3.1 and the zym gene on one recombinant chromosome 3.

In one embodiment the cultivated watermelon plant or plant part comprising the CVYV-resistance conferring locus cyv_3.1 as found in seeds deposited under accession numbers NCIMB 42449 or NCIMB 42450 or NCIMB 42666 and further comprise the zym gene.

In one embodiment the cultivated watermelon plant or plant part comprising the introgression fragment (comprising cyv_3.1) as found in seeds deposited under accession numbers NCIMB 42449 or NCIMB 42450 or NCIMB 42666, or a smaller fragment thereof (which retains locus cyv_3.1) and further comprise the zym gene.

In one aspect the diploid watermelon plants (and seeds from which the plants can be grown) according to the invention are inbred lines, produced by selfing several times.

In another aspect the diploid watermelon plants (and seeds from which the plants can be grown) according to the invention are F1 hybrids produced by crossing two diploid inbred lines according to the invention and collecting the seeds from the cross.

Plants grown from the deposited seeds were also tested for CGMMV (Cucumber Green Mottle Virus) resistance, but were susceptible, indicating that cyv_3.1 does not confer CGMMV resistance.

Tetraploid Cultivated Watermelon Plants, and Plant Parts, Comprising cyv_3.1 (or a Variant Thereof)

Seedless triploid watermelon production involves using pollen from diploid male parent plants to fertilize flowers of tetraploid (2n=4x=44) maternal parent plants. Pollination of the tetraploid flowers with diploid pollen leads to F1 seeds which are triploid (Kihara, 1951, Proceedings of American Society for Horticultural Science 58: 217-230; Eigsti 1971, Hort Science 6: 1-2). The triploid hybrid plants, grown from these F1 seeds, are self-infertile as they produce sterile pollen due to chromosome imbalance (Fehr, 1987). The triploid hybrids, therefore, need to be pollinated by a diploid pollenizer to produce watermelon fruit. Triploid plants are, therefore, interplanted with pollenizer plants for fruit production. The "seedless" fruit produced after pollination on the triploid hybrid plant are often not truly seedless, but may contain some undeveloped, small, pale seeds, which are edible.

Thus, to produce such seedless triploid varieties, a tetraploid female parent line (preferably an inbred line) and a diploid male parent line (preferably an inbred line) are crossed. The seeds produced in the fruits of the tetraploid parent via cross pollination are triploid, having two chromosome sets from the tetraploid mother and one chromosome set from the diploid father. These seeds are harvested and sold as triploid varieties. The triploid plants grown from these seeds still need pollen to induce fruit set (provided by a pollenizer), but the fruits produced are seedless watermelon fruits.

In one aspect a tetraploid watermelon plant is provided comprising four recombinant chromosomes 3, i.e. each comprising the introgression fragment from a wild watermelon comprising cyv_3.1. Thus, the tetraploid plant comprises four copies of cyv_3.1. When it is crossed with a diploid male parent line comprising two copies of cyv_3.1, the resulting triploid seeds comprise three copies of cyv_3.1.

To make such a tetraploid plant, any of the CVYV-resistant diploid plants described above, which are homozygous for the introgression fragment, may be used as starting material to generate tetraploid plants. Chromosome doubling techniques known to the skilled person may be used to generate a tetraploid plant from such diploid plants. For example Noh et al. (2012) Hort. Environ. Biotechnol. 53(6): 521-529, evaluated different methods of generating tetraploid watermelons. In all methods an antimitotic agent is used, such as colchicine, dinitoalanine, or oryzalin, in order to induce chromosome doubling. Optionally tissue culture may be used to generate tetraploid plants from plant parts. To verify that plants are tetraploid chromosome number can be confirmed. Ploidy can be easily determined by chromosome counting or flow cytometry or other known methods (Sari et al. 1999, Scientia Horticulturae 82: 265-277, incorporated herein by reference).

Thus, in one aspect of the invention (seed of) a CVYV-resistant tetraploid cultivated watermelon plant of the species *Citrullus lanatus* ssp. *vulgaris* is provided, wherein said plant comprises an introgression fragment from a wild watermelon plant on chromosome 3, whereby said introgression fragment confers CVYV-resistance due to the presence of the cyv_3.1 locus and whereby the recombinant chromosome 3 is present in four copies.

The introgression fragment is detectable by (or comprises) a marker selected from the group consisting of:

a) a Guanine (G) at nucleotide 76 of SEQ ID NO: 2 (SNP_02) or of a sequence comprising at least 90%, 91%, 92%, 93%, 94%, 95%, 96%, 97%, 98% or 99% sequence identity to SEQ ID NO: 2; and/or
b) a Cytosine (C) at nucleotide 76 of SEQ ID NO: 3 (SNP_03) or of a sequence comprising at least 90%, 91%, 92%, 93%, 94%, 95%, 96%, 97%, 98% or 99% sequence identity to SEQ ID NO: 3; and/or
c) a wild watermelon-genome-specific molecular marker within 5 Mb, 3 Mb, 2 Mb, 1 Mb, 0.5 Mb, 0.1 Mb, 74 kb, 50 kb, 20 kb, 10 kb, 5 kb, 2 kb, 1 kb or less of SNP_02 or SNP_03.

As mentioned, the tetraploid plant comprises four copies of said recombinant chromosome 3.

Thus, in one embodiment the tetraploid watermelon plant above comprises:
a) a tetraploid genotype GGGG (Guanine/Guanine/Guanine/Guanine) for nucleotide 76 of SEQ ID NO: 2 (SNP_02) or of a sequence comprising at least 90%, 91%, 92%, 93%, 94%, 95%, 96%, 97%, 98% or 99% sequence identity to SEQ ID NO: 2; and/or
b) a tetraploid genotype CCCC (Cytosine/Cytosine/Cytosine/Cytosine) at nucleotide 76 of SEQ ID NO: 3 (SNP_03) or of a sequence comprising at least 90%, 91%, 92%, 93%, 94%, 95%, 96%, 97%, 98% or 99% sequence identity to SEQ ID NO: 3; and/or
c) a tetraploid genotype for the wild watermelon-genome-specific molecular marker within 5 Mb, 3 Mb, 2 Mb, 1 Mb, 0.5 Mb, 0.1 Mb, 74 kb, 50 kb, 20 kb, 10 kb, 5 kb, 2 kb, 1 kb or less of SNP_02 or SNP_03.

Genotyping of tetraploid plants or plant parts (cells, leaves, DNA, etc.) can be done in the same way as for diploids, using for example a KASP-assay to distinguish SNP genotypes, e.g. plants or parts comprising GGGG for SNP_02 can be distinguished from plants or parts comprising GGGA, GGAA, GAAA or AAAA for SNP_02 in their genome.

As the tetraploid is made by doubling the chromosomes of a CVYV resistant diploid described further above, the aspects described for the diploid above apply to the tetraploid as well. For example, the tetraploid may also comprise the zym gene in coupling phase on the recombinant chromosome 3 and may thus comprise four copies of cyv_3.1 (or a variant thereof) and four copies of zym. Likewise haplotype A or haplotype B may be present in four copies.

So, from the above diploids the following tetraploids can be derived:

42449 and NCIMB 42450, or progeny thereof (e.g. comprising a smaller introgression fragment) are used to make tetraploids. These plants do not comprise the zym gene and are ZYMV susceptible.

In one aspect the diploid, CVYV resistant plants of which seeds were deposited under accession numbers NCIMB 42666, or progeny thereof (e.g. comprising a smaller introgression fragment) are used to make tetraploids.

In another aspect a cultivated watermelon plants comprising a cyv_3.1 gene from a different wild watermelon, such as from PI189318 or others, is used to make a tetraploid CVYV resistant plant.

Also, plants comprising both cyv_3.1 (or a variant) and the zym gene can be used to make tetraploids. The cyv_3. (or a variant thereof) can be easily combined with the zym gene, as e.g. found in PI595203, by traditional breeding techniques and selecting recombinants, optionally with the assistance of markers described herein, comprising both cyv_3.1 and zym on chromosome 3. PI595203 is available at the USDA, ARS, National Genetic Resources Program, Germplasm Resources Information Network—(GRIN).

Therefore, in one aspect a tetraploid watermelon plant (and seed from which the plant can be grown) is provided herein, comprising the CVYV-resistance conferring locus as found in NCIMB 42449 or NCIMB 42450 or NCIMB42666 or in PI189318 or other wild watermelons and optionally comprising the zym gene.

In one aspect the tetraploid watermelon plants (and seeds from which the plants can be grown) according to the invention are inbred lines, produced by selfing several times. In one aspect the plants are suitable as parent lines for triploid seed production, described below.

Seeds from which such tetraploid plants can be grown are encompassed herein. Also plant parts of the tetraploid plants according to the invention are encompassed herein, such as cells, pollen, flowers, fruits, leaves, stems, etc. Fruits are preferably marketable fruits. The brix is preferably at least 6.0, 7.0, 8.0 or least 9.0, preferably at least 10.0, more preferably at least 11.0 or more. Fruit color may be any color, such as red, dark red, scarlet red, coral red, orange, salmon, pink, pinkish red, yellow, canary yellow or white. Preferably the fruit flesh color is uniform.

In one aspect the tetraploid plant of the invention is a vegetative propagation.

The tetraploid plants may be selfed one or more time, but they may also be crossed to another tetraploid watermelon plant. If that other tetraploid watermelon plant lacks

| SNP marker and gene on chromosome 3 | Diploid SNP genotype → tetraploid SNP genotype | Diploid SNP genotype → tetraploid SNP genotype |
| --- | --- | --- |
| SNP_01 | GG → GGGG | AA → AAAA |
| SNP_02 | GG → GGGG | GG → GGGG |
| SNP_03 | CC → CCCC | CC → CCCC |
| Optionally zym gene | zym/zym → zym/zym/zym/zym | zym/zym → zym/zym/zym/zym |
| Optionally SNP_04 | GG → GGGG | GG → GGGG |

The CVYV resistant tetraploid is preferably selfed a number of times, to produce an inbred tetraploid, which can be used as female parent in the production of triploid seeds.

In one aspect the diploid, CVYV resistant plants of which seeds were deposited under accession numbers NCIMB cyv_3.1, the F1 produced by the cross contains only two copies of cyv_3.1. If such a plant is crossed again with a tetraploid plant lacking cyv_3.1, progeny with only one copy of cyv_3.1 can be generated. Similarly if such a plant is selfed, progeny with one or three copies of cyv_3.1 can be generated. Thus, a tetraploid watermelon comprising 3, 2 or only 1 copy of cyv_3.1 are also encompassed herein.

Triploid Cultivated Watermelon Plants, and Plant Parts, Comprising cyv_3.1 (or a Variant Thereof)

In one aspect the CVYV-resistant tetraploid plant described above is used as female parent and is pollinated with pollen of a CVYV-resistant diploid male parent (also as described above) and the seeds from the cross are harvested. These seeds are triploid, i.e. they comprise three copies of the cyv_3.1 locus of the invention. Plants grown from these seeds are CVYV resistant and produce seedless watermelon fruits (triploid fruits). Optionally plants are also ZYMV resistant, i.e. comprise the zym gene.

Thus all aspects described above for the diploids and tetraploid plants of the invention apply to the triploid seeds and plants grown from such seeds. So for example, in one aspect the cyv_3.1 locus is the cyv_3.1 locus as found in seeds deposited under NCIMB 42449 or NCIMB 42450 or NCIMB 42666. But it may also be the cyv_3.1 gene as found in wild watermelons, such as PI189318 or others. In another aspect the introgression fragment (comprising the cyv_3.1 locus) as found in seeds deposited under NCIMB 42449 or NCIMB 42450 or NCIMB 42666 is encompassed herein, or a smaller fragment thereof, which smaller fragment retains the cyv_3.1 locus. But also other variants of cyv_3.1 are encompassed herein, e.g. from other wild watermelon accessions.

Seeds from which triploid CVYV-resistant plants can be grown are an embodiment herein, as are plant parts grown from such seeds, as well as seedless watermelon fruits produced by these plants.

Triploid, seedless fruits are preferably marketable. Preferably they have an average brix of at least 6.0, 7.0, 8.0 or preferably at least 9.0, preferably at least 10.0, more preferably at least 11.0.

Fruits may be of any size, shape, color and rind pattern. Preferably fruit flesh color at maturity is uniform. In one aspect fruit flesh is red or dark red.

The average fruit weight of a triploid hybrid comprising cyv_3.1 (or a variant thereof) in three copies may be equal to or above 2, 3, 4, 5, 6, 7, 8, 9, 10, 11, 12, 13 or 14 kg. In another embodiment average fruit weight of a triploid hybrid comprising cyv_3.1 (or a variant thereof) in three copies may be equal to or less than 5 kg, e.g. 4, 3, 2, 1.5 or 1 kg or even less.

Seedless fruits may be of any shape (e.g. elongate, oval, blocky, spherical or round), fruit surface (furrow, smooth), flesh color (red, dark red, scarlet red, coral red, orange, salmon, pink, pinkish red, yellow, canary yellow or white), rind color (e.g. light green; dark green; green-striped with narrow, medium or wide stripes; grey types; with or without spotting; Golden yellow), rind thickness, rind toughness, rind pattern (e.g. striped, non-striped, netted), flesh structure/flesh firmness, lycopene and/or vitamin content, different sugar to acid ratios, fruit flavour, etc.

Thus, the CVYV-resistance conferring cyv_3.1 locus (or variant) may be used to breed a range of seedless varieties, producing fruits of different shapes and sizes, etc. by traditional breeding. See Guner and Wehner 2004, Hort Science 39(6): 1175-1182, in particular pages 1180-1181 describing genes for fruit characteristics. Generally important breeding objectives are early maturity, high fruit yield, high internal fruit quality (good uniform color, high sugar, proper sugar: acid ratio, good flavor, high vitamin and lycopene content, firm flesh texture, non-fibrous flesh texture, freedom from defects such as hollow heart, rind necrosis, blossom-end rot or cross stitch and good rind characteristics and cracking-resistance).

In one aspect the triploid plant of the invention is a vegetative propagation.

Vegetative Propagations and Cell or Tissue Cultures

The above diploid plants, tetraploid plants or triploid plants can also be reproduced vegetatively (clonally) and such vegetatively propagated plants, or 'vegetative propagations' are an embodiment of the invention. They can easily be distinguished from other watermelon plants by one or more (or all) of the markers linked to cyv_3.1 (or a variant thereof) and/or phenotypically.

Vegetative propagations can be made by different methods. For example one or more scions of a plant of the invention may be grafted onto a different rootstock, e.g. a biotic or abiotic stress tolerant rootstock.

Other methods include in vitro cell or tissue culture methods and regeneration of vegetative propagations from such cultures. Such cell or tissue cultures comprise or consist of various cells or tissues. In one aspect such a cell or tissue culture comprises or consists of vegetative cells or vegetative tissues.

In another aspect a cell or tissue culture comprises or consists of reproductive cells or tissues, such as anthers or ovules. Such cultures can be treated with chromosome doubling agents to make e.g. double haploid plants, or they can alternatively be used to make haploid plants (e.g. to make diploids from a tetraploid or to make haploids from a diploid).

An in vitro cell or tissue culture may, thus, comprise or consist of cells or protoplasts or plant tissue from a plant part selected from the group consisting of: fruit, embryo, meristem, cotyledon, pollen, ovule, leaf, anther, root, root tip, pistil, flower, seed, stem. Also parts of any of these are included, such as e.g. only the seed coat (maternal tissue).

Thus, in one aspect of the invention a cell culture or a tissue culture of cells of a plant comprising one, two, three or four copies of cyv_3.1 (or a variant), all as described above, is provided. As mentioned, a cell culture or a tissue culture comprises cells or protoplasts or plant tissue from a plant part of a plant comprising cyv_3.1 may be comprise or consist of cells or tissues selected from the group consisting of: embryo, meristem, cotyledon, pollen, leaf, anther, root, root tip, pistil, flower, seed, stem; or parts of any of these.

Also provided is a watermelon plant regenerated from such a cell culture or tissue culture, wherein the regenerated plant (or progeny thereof, e.g. obtained after selfing the regenerated plant) comprises the cyv_3.1 locus (or a variant thereof). Therefore, in one aspect the watermelon plant comprising cyv_3.1 (or a variant thereof) in one or more copies is a vegetatively propagated watermelon plant.

In a different aspect the cells and tissues of the invention (and optionally also the cell or tissue culture), comprising cyv_3.1 (or a variant thereof) in one or more copies, are non-propagating cells or tissues.

Methods and Uses of QTL cyv_3.1 (or a Variant) and/or of Markers Linked to cyv_3.1 (or to a Variant Thereof)

The recessive cyv_3.1 locus of the invention (or a variant thereof), i.e. the introgression fragment comprising the locus, can be transferred into, or introduced into, any other cultivated watermelon plant, by e.g. making crosses with plants of the invention, e.g. plants grown from the deposited seeds, or with vegetatively propagated plants of the invention, or by identifying wild watermelon plants comprising the cyv_3.1 (or a variant thereof) and introgressing cyv_3.1

(or a variant thereof) from such a wild accession into cultivated watermelon as described herein.

For example wild accessions of watermelon can be screened with one or more markers linked to the cyv_3.1 locus (e.g. SNP_02 and/or SNP_03 and/or one or more other markers linked to cyv_3.1) to identify putative wild accessions comprising cyv_3.1 or a variant thereof. Such accessions can optionally or alternatively also be screened phenotypically in a CVYV resistance assay and/or they can be crossed with cultivated watermelon plants and descendants of the cross can be screened for the CVYV resistance marker genotype and/or CVYV-resistance phenotype. The skilled person can, therefore, identify the QTL cyv_3.1 or a variant thereof in other wild watermelon accessions, transfer it into cultivated watermelon onto chromosome 3, e.g. by backcrossing 4, 5, 6, 7 or more times to cultivated watermelon lines to generate diploid watermelon plants of the invention. These can then be used to generate tetraploids and triploids as described herein.

Thus, the CVYV resistance conferred by cyv_3.1, or a variant thereof, can be crossed into different genetic backgrounds of cultivated watermelon by e.g. using seed deposited herein as a source of cyv_3.1, as described elsewhere herein, or by identifying the cyv_3.1 (or a variant thereof) in wild watermelon accessions and (back)crossing it into cultivated watermelon.

The cyv_3.1 (or a variant) can be introduced into other watermelon plants lacking cyv_3.1 (or a variant) using known breeding methods. Known breeding methods can be used alone or in combination, such as (but not limited to) recurrent selection, pedigree breeding, backcross breeding, inbred development, hybrid testing, marker assisted breeding, etc. Progeny are then selected which retain cyv_3.1 (or a variant) using one or more of the markers provided herein and/or CVYV resistance (when no dominant WT allele is present). Thus, selection of progeny plants having cyv_3.1 (or a variant) can be done by phenotypic selection of CVYV resistance in plants selfed one or more times and by discarding plants which are CVYV susceptible. For example, if progeny which segregate for CVYV resistance are inoculated or planted in a CVYV infested area, CVYV resistant plants can be easily identified.

Thus, in one aspect a method of generating a diploid cultivated watermelon of the species *Citrullus lanatus* ssp. *vulgaris* is provided, wherein said plant comprises an introgression fragment from a wild watermelon plant on chromosome 3, whereby said introgression fragment comprises a CVYV-resistance conferring locus, is provided, comprising the steps of: Crossing a wild watermelon plant comprising a CVYV resistance-conferring locus on chromosome 3 with a diploid cultivated watermelon plant and selecting progeny of said cross which comprise a genome of cultivated watermelon and an introgression fragment on chromosome 3 from the wild watermelon plant, whereby said introgression fragment comprises the CVYV resistance conferring locus.

The presence of the CVYV resistance conferring locus in the wild watermelon plant and/or in the progeny may be determined phenotypically using a CVYV resistance assay and/or on a molecular level, by detecting the presence of one or more of the markers described herein linked to cyv_3.1 (or a variant), e.g. one or more markers selected from the group consisting of:

a) a Guanine (G) at nucleotide 76 of SEQ ID NO: 2 (SNP_02) or of a sequence comprising at least 900/o, 91%, 92%, 93%, 94%, 95%, 96%, 97%, 98% or 99% sequence identity to SEQ ID NO: 2; and/or b) a Cytosine (C) at nucleotide 76 of SEQ ID NO: 3 (SNP_03) or of a sequence comprising at least 90%, 91%, 92%, 93%, 94%, 95%, 96%, 97%, 98% or 99% sequence identity to SEQ ID NO: 3; and/or (optionally)

c) a wild watermelon-genome-specific molecular marker within 5 Mb, 3 Mb, 2 Mb, 1 Mb, 0.5 Mb, 0.1 Mb, 74 kb, 50 kb, 20 kb, 10 kb, 5 kb, 2 kb, 1 kb or less of SNP_02 or SNP_03.

The introgression fragment can also be transferred to other diploid cultivated watermelon plants, e.g. to combine CVYV resistance with other traits. Thus, in another aspect a method of generating a diploid cultivated watermelon of the species *Citrullus lanatus* ssp. *vulgaris* is provided, wherein said plant comprises an introgression fragment from a wild watermelon plant on chromosome 3, whereby said introgression fragment comprises a CVYV-resistance conferring locus, is provided, comprising the steps of:

Crossing a diploid cultivated watermelon plant comprising a CVYV resistance-conferring locus on chromosome 3 (as described above) with another diploid cultivated watermelon plant, especially a plant lacking a CVYV resistance conferring locus on chromosome 3, and selecting progeny of said cross (e.g. F1, F2, F3 or further selfing progeny or backcross progeny) which comprise a genome of cultivated watermelon and an introgression fragment on chromosome 3 from the wild watermelon plant, whereby said introgression fragment comprises the CVYV resistance conferring locus. The progeny may also be a result of one or more backcrosses optionally combined with one or more selfings, e.g. BC1, BC1S1, BC1S2, BC2, BC2S1, BC3, etc. Again, the presence of the introgression fragment in the progeny may be determined using one or more of the markers described and/or CVYV resistance assays.

Also a screening method for selecting or identifying watermelon seeds, plants or plant parts or DNA from such seeds, plants or plant parts comprising in their genome an introgression fragment on chromosome 3 comprising a CVYV-resistance conferring locus is provided, said method comprises: Screening watermelon seeds, plants or plant parts (e.g. cells) or DNA from such seeds, plants or plant parts for the presence of one or more markers described herein linked to cyv_3.1 (or a variant), e.g. one or more markers selected from the group consisting of:

a) a Guanine (G) at nucleotide 76 of SEQ ID NO: 2 (SNP_02) or of a sequence comprising at least 90%, 91%, 92%, 93%, 94%, 95%, 96%, 97%, 98% or 99% sequence identity to SEQ ID NO: 2; and/or b) a Cytosine (C) at nucleotide 76 of SEQ ID NO: 3 (SNP_03) or of a sequence comprising at least 90%, 91%, 92%, 93%, 94%, 95%, 96%, 97%, 98% or 99% sequence identity to SEQ ID NO: 3; and/or c) a wild watermelon-genome-specific molecular marker within 5 Mb, 3 Mb, 2 Mb, 1 Mb, 0.5 Mb, 0.1 Mb, 74 kb, 50 kb, 20 kb, 10 kb, 5 kb, 2 kb, 1 kb or less of SNP_02 or SNP_03.

The watermelon seeds, plants or plant parts may be haploid, doubled-haploid, diploid, triploid or tetraploid. Obviously, screening for the presence of one or more markers may involve screening (detection) of several copies of the marker, e.g. four copies of Guanine (G) of SNP_02 in a tetraploid. Likewise, alternatively or in addition, the screening for the absence of the WT (susceptible) SNP genotype is encompassed herein. So, when referring to a diploid plant, plant part or DNA comprising a Guanine (G) at nucleotide 76 of SEQ ID NO: 2 (SNP_02) or in a sequence comprising at least 90%/0, 91%, 92%/0, 93%, 94%, 95%, 96%, 97%, 98% or 99% sequence identity to SEQ ID NO:

2, the marker assay alternatively or in addition may detect the presence or absence of Adenine (A) at nucleotide 76 of SEQ ID NO: 2 (SNP_02) or of a sequence comprising at least 90%/0, 91%, 920/0, 93%, 94%, 95%, 96%, 97%, 98%/0 or 99% sequence identity to SEQ ID NO: 2.

Optionally the method further comprises selecting one or more seeds, plants or plant parts comprising the introgression fragment in one copy (e.g. for haploids or diploids), in two copies (e.g. for diploids or doubled-haploids), in three copies (e.g. for triploids) or in four copies (e.g. for tetraploids).

The molecular markers described herein may be detected according to standard method. For example SNP markers can easily be detected using a KASP-assay (see www.kpbioscience.co.uk) or other SNP genotyping assays. For developing a KASP-assay, for example 70 base pairs upstream and 70 base pairs downstream of the SNP can be selected and two allele-specific forward primers and one allele specific reverse primer can be designed. See e.g. Allen et al. 2011, Plant Biotechnology J. 9, 1086-1099, especially p 097-1098 for KASP assay method.

Thus, in one aspect, the SNP markers and the presence/absence of the marker associated with cyv_3.1 is determined using a KASP assay, but equally other SNP genotyping assays can be used. For example, a TaqMan SNP genotyping assay, a High Resolution Melting (HRM) assay, SNP-genotyping arrays (e.g. Fluidigm, Illumina, etc.) or DNA sequencing may equally be used.

In a different aspect a method of generating a tetraploid cultivated watermelon of the species *Citrullus lanatus* ssp. *vulgaris* is provided, wherein said plant comprises an introgression fragment from a wild watermelon plant on chromosome 3, whereby said introgression fragment comprises a CVYV-resistance conferring locus, comprising the steps of:

Doubling the chromosomes of a diploid cultivated watermelon or part thereof, said diploid being CVYV resistant due to the presence of an introgression fragment on chromosome 3 comprising a CVYV-resistance conferring locus in homozygous form, as described elsewhere, and identifying (or selecting) a tetraploid plant or plant part and optionally regenerating a whole plant therefrom.

The tetraploid plant is optionally further selfed one or more times to produce an inbred tetraploid line, comprising four copies of cyv_3.1 or a variant thereof.

See e.g. http://cuke.hort.ncsu.edu/cucurbitlwmelon/seedless.html for doubling the chromosome by colchicine treatment and tetraploid identification.

Again, the presence of the cyv_3.1 or variant thereof can be determined by detecting one or more or all of the linked markers.

A method for generating a tetraploid inbred plant having CVYV resistance is provided, comprising the steps of:
a) providing a diploid inbred line comprising an introgression fragment from a wild watermelon plant on chromosome 3, said introgression fragment comprising a CVYV resistance conferring locus, in homozygous form, and
b) doubling the chromosomes of said inbred line or plant part of the line to generate a tetraploid line or tetraploid plant part and regenerating a tetraploid plant of the line, and
c) selfing the tetraploid line for several generations.

In step a) the diploid plant may be any diploid plant of the invention as described above, e.g. it may be a plant derived from seed deposited under NCIMB 42449 or NCIMB 42450 or NCIMB 42666, or progeny of any of these, or may be a diploid plant into which cyv_3.1 from seed deposit NCIMB 42449 or NCIMB42450 or NCIMB 42666 has been transferred by crossing. The diploid may also be new diploid plant generated by introgression cyv_3.1 or a variant thereof from a wild CVYV resistant watermelon into cultivated watermelon. The introgression may for example be from PI189318 or other wild watermelon accessions.

In yet another aspect, a method for generating triploid hybrid watermelon plants of the species *Citrullus lanatus* ssp. *vulgaris* is provided, comprising:

Crossing a tetraploid female parent line comprising four copies of cyv_3.1 (or a variant thereof) with a diploid male parent line comprising two copies of cyv_3.1 (or a variant thereof) and collecting seeds produced on the female parent line. Optionally the harvested seeds may be dried.

Pollination of the tetraploid female line may be by hand or by insects (e.g. bees) in isolation blocks. To ensure pollination of the tetraploid female flowers with pollen from the male diploid, different methods can be used, such as collecting male flowers by hand and hand-pollinating female flowers, followed by covering the pollinated flower. Alternatively, all male (staminate) flowers that develop on the tetraploid plants may be removed to ensure pollination of the pistillate flowers on the tetraploid plants with diploid pollen. When the fruits on the tetraploid plants are mature, they are harvested and the triploid F1 hybrid seeds (resulting from cross-pollination) are collected. These may then be sorted (e.g. by size), dried, optionally treated, and packaged for sale. Thus packages or containers comprising or consisting of seeds obtained by the above method are an embodiment herein.

In one embodiment a method for producing seedless triploid fruits is provided, comprising:
a) interplanting triploid hybrid watermelon plants comprising three copies of cyv_3.1 or a variant thereof and diploid pollenizer plants,
b) allowing pollination of the female flowers on the triploid hybrid plants to occur, and, optionally,
c) harvesting the fruits from the triploid hybrid plants.

Thus, for seedless fruit production, the triploid CVYV resistant hybrid according to the invention may be interplanted with a suitable diploid pollenizer, such as for example Jenny or Polimax may be used, or Super-pollenizers (SP-1, SP-2, SP-3, SP-4, SP-5), Sidekick, Escort-4, Companion or others. Optionally, the pollenizer may be a dual purpose pollenizer as described in WO2012/069539 A1. The diploid pollenizer should produce sufficient pollen at the right time of the day and for an appropriate period of time to induce fruit set in triploid hybrids. The pollenizer plants may be hybrid diploids (F1 diploids) or open pollinated (OP) pollenizers. Fruit are then harvested from the triploid plants of the invention.

The triploid plants may be grafted onto different rootstocks. The method is preferably carried out in the open field. Interplanting in one field may be either done by seeding or transplants of the pollenizer and triploids. Various interplanting methods can be used, as known in the art and various ratios of pollenizer: triploid hybrid may be used. One row of pollenizer plants may for example be present at least every 2, at least every 3 or at least every 4 rows of triploids, but other methods of interplanting may also be used. Pollination is usually done by bees, and bee hives can be provided to the fields unless sufficient wild bees are naturally present. Pollination can also be performed by manual or mechanical means. Harvest at maturity may be done by hand or mechanized.

The triploid fruits, containing three copies of cyv_3.1 (or a variant thereof), are seedless. The fruits may be harvested for fresh consumption or for processing. Containers comprising or consisting of a plurality of such fruits or fruit parts are a further embodiment of the invention. The harvested fruits can, thus, be sorted, packaged in containers etc. Containers comprising or consisting of triploid fruits preferably comprise or consist of marketable fruits, comprising three copies of cyv_3.1 (or a variant) in their genome. Also containers comprising fruit parts and food or feed products comprising fruit parts are encompassed herein.

Uses According to the Invention

The use of cyv_3.1 (or a variant thereof) for generating CVYV-resistant cultivated watermelon plants, producing marketable fruits, is one aspect of the invention. Likewise the use of any of the markers linked to cyv_3.1 (or a variant thereof) in identifying and/or selecting plants or plant parts or progeny comprising or retaining cyv_3.1 (or a variant thereof) is encompassed.

In one aspect also the use of a diploid or doubled-haploid plant according to the invention as a male or female parent is provided, whereby the plant is crossed with another watermelon plant or is allowed to self-fertilize to produce progeny.

In one aspect the use of a tetraploid plant according to the invention as a male or female parent is provided, whereby the plant is crossed with another watermelon plant (e.g. with a diploid male parent) or is allowed to self-fertilize to produce progeny. Especially the use of a tetraploid as a female parent in hybrid triploid watermelon seed production (i.e. F1 seed production) is encompassed.

In another aspect the use of triploid plant according to the invention in triploid seedless fruit production is provided.

Seeds and Plant Parts and Progeny

It is understood that it is also an object of the invention to provide seeds from which the diploid, triploid or tetraploid plants described herein can be grown. Also seedlings, scions and rootstocks, as well as cells and tissues of the diploid, doubled-haploid, triploid or tetraploid plants of the invention are encompassed herein. Such plant parts comprise cyv_3.1 (or a variant) according to the invention. A plant part of the plant may e.g. be selected from a scion, fruit, pollen, ovule, stem, cotyledon, leaf, cell, embryo, meristem, anther, root, root tip, pistil, flower, and/or seed.

Also progeny of any of the plants according to the invention are provided herein, such as seeds obtainable by crossing a plant comprising cyv_3.1 (or a variant) described herein with another watermelon plant and/or by selfing a plant according to the invention to produce F1 seeds, and further generation progeny (F2, F3, etc.). The presence of cyv_3.1 (or a variant) in the progeny can be determined by CVYV resistance assays and/or markers analysis.

Watermelon plants obtained (derived), or obtainable (derivable), from plants according to the invention (e.g. from plants comprising cyv_3.1 or a variant thereof) include plants obtained by breeding methods, such as selfing, crossing, backcrossing, recurrent selection, double haploid production, marker assisted selection, clonal propagations, transformants, etc., whereby the derived plants comprise at least one recombinant chromosome 3 comprising cyv_3.1 (or a variant) according to the invention.

In one aspect a watermelon plant is provided, of which a representative number of seeds has been deposited under accession number NCIMB 42449 or NCIMB 42450 or NCIMB 42666, or progeny of any such plants, e.g. obtained by crossing and/or selfing. In one aspect a watermelon seed is provided, of which a representative number of seeds has been deposited under accession number NCIMB 42449 or NCIMB 42450 or NCIMB 42666. Also pollen, an ovule, cells, tissues, vegetative propagations obtained from these plants, or from the progeny thereof, are provided. In one aspect progeny retain the cyv_3.1 of the plants of which seeds were deposited under NCIMB 42449 or NCIMB 42450 NCIMB 42666. In one aspect progeny retain the introgression fragment on chromosome 3 (comprising cyv_3.1) of the plants of which seeds were deposited under NCIMB 42449 or NCIMB 42450 NCIMB 42666, or a smaller fragment of the introgression fragment, whereby the smaller fragment retains the CVYV resistance conferring locus (cyv_3.1).

Fine-Mapping, Sequencing and Allelism Tests

The cyv_3.1 locus was found in the region between about 2.50 Mb and about 12.8 Mb of chromosome 3, see FIG. 1. Fine-mapping can be carried out using methods known in the art to determine the exact position of the locus. For example recombinant lines can be generated comprising smaller parts of the introgressed region and CVYV assays can then be used to determine which fragment still confers resistance against CVYV (and thus retains the locus). Alternatively the region can also be sequenced to identify candidate resistance genes. Using such methods or similar methods markers more closely linked to the cyv_3.1 locus (or variant) can be identified, e.g. wild watermelon-genome-specific molecular marker linked to cyv_3.1 (or a variant) can be identified, within a physical distance of 5 Mb, 3 Mb, 2 Mb, 1 Mb, 0.5 Mb, 0.1 Mb, 74 kb, 50 kb, 20 kb, 10 kb, 5 kb, 2 kb, 1 kb or less of SNP_02 or SNP_03.

Similarly, any CVYV resistant wild watermelon accessions, e.g. PI189318 or others, can be crossed with cultivated CVYV susceptible watermelon to generate a new mapping population and to determine whether the CVYV resistance is conferred by cyv_3.1 or a variant thereof, i.e. if a CVYV resistance QTL is mapped to the same region of chromosome 3, the wild accession clearly contains the cyv_3.1 locus or a variant thereof.

If two watermelon plants both have CVYV resistance and it is not clear if the resistance is caused by the same QTL, different methods can be used to verify whether the same locus (i.e. cyv_3.1 or a variant) is involved. As mentioned, marker tests and/or sequencing and/or QTL mapping or fine-mapping can be used to determine whether a resistance-conferring introgression fragment from a wild watermelon is present in the region of chromosome 3. Alternatively or in addition an allelism test can be carried out, i.e. the two plants can be crossed and segregation of the phenotype (CVYV resistance) in progeny plants can be analysed.

The following non-limiting Examples describe plants comprising cyv_3.1 according to the invention. Unless stated otherwise in the Examples, methods for conventional watermelon breeding are used, such as e.g. described in Maynard 2001, Watermelons—Characteristics, Production and Marketing, ASHS Press; Mohr H. C. Watermelon Breeding in Mark J. Bassett (editor) 1986 Breeding Vegetable Crops, AVI Publishing Company.

DEPOSIT INFORMATION

Nunhems B.V. has deposited seeds of a diploid cultivated watermelon line, comprising cyv_3.1 in homozygous form and producing fruits with a Crimson Sweet type rind under accession number NCIMB 42449 and seeds of a diploid cultivated watermelon line, comprising cyv_3.1 in homozygous form and producing fruits with a Jubilee type rind under accession number NCIMB 42450. The seeds were deposited by Nunhems B.V. on 18 Aug. 2015 at the NCIMB Ltd., Ferguson Building, Craibstone Estate, Bucksburn, Aberdeen AB21 9YA, UK. Access to the deposits will be available during the pendency of this application to persons determined by the Commissioner of Patent and Trademarks to be entitled thereto upon request.

Nunhems B.V. has deposited seeds of a diploid cultivated watermelon elite line, comprising cyv_3.1 in homozygous form and producing red fleshed fruits under accession number NCIMB42666. The seeds were deposited by Nunhems B.V. on 26 Sep. 2016 at the NCIMB Ltd., Ferguson Building, Craibstone Estate, Bucksburn, Aberdeen AB21 9YA, UK.

All seed deposits were made under the Budapest Treaty and making use of the Expert solution.

Subject to 37 C.F.R. § 1.808(b), all restrictions imposed by the depositor on the availability to the public of one or more deposits will be irrevocably removed upon the granting of the patent by affording access to the deposits. The deposits will be maintained for a period of 30 years, or 5 years after the most recent request, or for the enforceable life of the patent whichever is longer, and will be replaced if it ever becomes nonviable during that period. Applicant does not waive any rights granted under this patent on this application or under the Plant Variety Protection Act (7 USC 2321 et seq.).

EXAMPLES

Example 1: CVYV Resistance—QTL Mapping

Two F2 mapping populations were generated from crosses between wild watermelon accession and a CVYV susceptible inbred proprietary line. The populations were genotyped with >3000 SNPs.

Phenotyping of F3 lines was performed using a CVYV assay in climate cells in Italy. The first true expanded leaf (15 to 20 days after sowing) was inoculated by hand, with a second inoculation 4-5 days after the first one. Control plants were inoculated with buffer only.

A total of 14 plants per genotype was inoculated with inoculum containing CVYV (Almeria type strain), in two replicates and including Sugar Baby as susceptible control. A randomized block design was used. CVYV was maintained in frozen infected leaf tissue. To prepare inoculum pre-multiplication of the virus was carried out on susceptible cucumber variety Sheila. Fresh, young, symptomatic leaves of variety Sheila were then used to prepare the inoculum (1 gram fresh leaf per 5 ml 0.03M phosphate buffer, with active carbon and diatomaceous earth were crushed with a pestle and mortar on a bed of ice).

Inoculated plants were incubated with 12-14 hours light, day temperature 25 degrees Celsius and night temperatures 18 degrees Celsius. Leaves were scored for CVYV symptoms at regular intervals (e.g. 20 days post inoculation (dpi), 35 dpi, 50 dpi, 65 dpi). The susceptible control, Sugar Baby, must be severely symptomatic after 30 dpi. Individual plants were scored in three classes: a) susceptible-presence of symptoms on the leaves, b) resistant—no symptoms on the leaves, c) doubtful. At least 90% of the plants of a line had to be scored as 'resistant' for the line to be considered resistant.

QTL mapping revealed a major QTL for CVYV resistance on chromosome 3 in both mapping populations, which was named cyv_3.1.

To better localize the QTL more SNP markers were identified in the confidence interval. Three markers closely linked to the QTL were identified, see Table 1 (supra), termed SNP_01, SNP_02 and SNP_03.

TABLE 3

| SNP | Chromosome | Base position on chromosome 3 |
|---|---|---|
| SNP_01 | Chr_03 | 7,586,752 |
| SNP_02 | Chr_03 | 7,664,093 |
| SNP_03 | Chr_03 | 7,693,225 |

Example 2: Backcrossing of Cyv_3.1 into Elite Lines

Using marker assisted backcrossing, cyv_3.1 was backcrossed (4 to 6 backcrosses) into several elite lines and seeds of two elite lines were deposited under accession numbers NCIMB 42449 and NCIMB 42450.

Plants of NCIMB 42449 and NCIMB 42450, and selfing progeny thereof, were evaluated (phenotyped) for resistance against CVYV in two consecutive years in climate cells in Murcia, in the same way as described in Example 1.

Results are shown in Table 4 below:

| Plant line | Repetition | Nr. of plants | First evaluation (% of plants resistant) | Second evaluation (% of plants resistant) |
|---|---|---|---|---|
| 2014 phenotyping: | | | | |
| NCIMB42449 | 1 | 10 | 100 | 100 |
| NCIMB42449 | 2 | 10 | 100 | 100 |
| NCIMB42449 | 3 | 10 | 100 | 100 |
| NCIMB42450 | 1 | 10 | 80 | 80 |
| NCIMB42450 | 2 | 10 | 100 | 100 |
| Susceptible line | 1 | 10 | 0 | 0 |
| Susceptible line | 2 | 10 | 30 | 20 |
| Susceptible line | 1 | 10 | 40 | 0 |
| Susceptible line | 2 | 10 | 50 | 20 |
| Susceptible line | 3 | 10 | 40 | 10 |
| Sugar Baby (control) | Multiple | 50 | 22 | 0 |
| 2015 phenotyping: | | | | |
| Progeny of NCIMB42449 | 1 | 14 | 100 | 100 |
| Progeny of NCIMB42449 | 2 | 13 | 100 | 100 |
| Progeny of NCIMB42449 | 3 | 14 | 100 | 100 |
| Progeny of NCIMB42449 | 4 | 15 | 100 | 100 |
| Progeny of NCIMB42450 | 1 | 15 | 100 | 100 |
| Progeny of NCIMB42450 | 2 | 15 | 100 | 100 |
| Progeny of NCIMB42450 | 3 | 14 | 100 | 100 |
| Progeny of NCIMB42450 | 4 | 14 | 100 | 100 |
| Progeny of NCIMB42450 | 5 | 14 | 100 | 100 |
| Sugar Baby (control) | Multiple | 35 | 27 | 0 |

Example 3: Marker Validation

Validation of these markers over a collection of different watermelon material yielded the discovery of two haplotypes for CVYV resistance, whereby SNP_01 could distinguish the haplotypes. All commercial hybrids tested had the same genotype as Sugar Baby and were all CVYV susceptible.

TABLE 5

|  | SNP_01 | SNP_02 | SNP_03 | CVYV resistance |
|---|---|---|---|---|
| Inbred line - NCIMB 42666 | GG | GG | CC | Resistant |
| Inbred line - NCIMB 42449 | AA | GG | CC | Resistant |
| Inbred line - NCIMB42450 | AA | GG | CC | Resistant |
| SUGAR BABY | GG | AA | TT | Susceptible |

Example 4: ZYMV Resistance is an Independent Locus on Chromosome 3

As from the literature it was known that ZYMV resistance is also located on chromosome 3, the inventors wanted to know if the CVYV resistant plants were also ZYMV resistant. They inoculated NCIMB 42449 and NCIMB 42450 with either the European or the US strain of ZYMV. They also re-analyzed the SNP marker data for the SNP published to be linked to the zym gene, referred to as SNP_04 herein.

TABLE 6

|  | SNP_01 | SNP_02 | SNP_03 | SNP_04 | CVYV resistance | ZYMV resistance |
|---|---|---|---|---|---|---|
| Inbred line - not deposited | GG | GG | CC | GG | Resistant | Resistant |
| Inbred line - NCIMB 42449 | AA | GG | CC | TT | Resistant | Susceptible |
| Inbred line - NCIMB42450 | AA | GG | CC | TT | Resistant | Susceptible |
| SUGAR BABY | GG | AA | TT | TT | Susceptible | Susceptible |

The results showed that cyv_3.1 and zym are independent loci on chromosome 3 and that SNP_04 can be used to differentiate between ZYMV resistant and susceptible plants.

Example 5: Tetraploid Lines

NCIMB 42449 and NCIMB 42450 were both used to generate CVYV resistant tetraploid lines using colchicine treatment. For NCIMB 42449 five putative tetraploid lines were made, while for NCIMB 42450 ten putative tetraploid lines were made.

Example 6: Screening of Wild Watermelon Accessions

Progeny of wild, diploid, watermelon accessions originating e.g. from the US GRIN collection were screened for CVYV resistance and for their SNP genotype for SNP_01, SNP_02 and SNP_03.

One line, derived from PI189318 was found to have the following SNP genotype and the following resistance phenotype:

TABLE 7

|  | SNP_01 | SNP_02 | SNP_03 | CVYV resistance |
|---|---|---|---|---|
| PI189318 | GG | GG | CC | Resistant |

This wild watermelon can, therefore, be used to introgress cyv_3.1 into cultivated watermelon, e.g. by backcrossing.

Optionally an allelism test can be carried out, by crossing PI189318 with plants grown from seeds deposited herein to confirm that PI189318 contains the cyv_3.1 gene.

The invention claimed is:

1. A diploid cultivated watermelon plant of the species *Citrullus lanatus* ssp. *vulgaris*, or part thereof, comprising an introgression fragment from a wild watermelon plant on chromosome 3, whereby said introgression fragment comprises a (Cucumber Vein Yellowing Virus) CVYV-resistance conferring locus and whereby the introgression fragment comprises the following markers:

a) a Guanine (G) at nucleotide 76 of SEQ ID NO: 2 (SNP_02); and b) a Cytosine (C) at nucleotide 76 of SEQ ID NO: 3 (SNP_03), wherein the CVYV resistance conferring locus is obtainable from seeds deposited under accession number NCIMB42449, NCIMB42450, NCIMB42666, or from wild accession PI189318.

2. The plant according to claim 1, wherein the introgression fragment is a fragment comprising the region starting at 2.50 Mb and ending at 12.80 Mb of chromosome 3, or a part thereof, wherein the part is at least 5 kb in size.

3. The plant according to claim 1, wherein the plant produces fruits comprising a degree brix of at least 7.0.

4. The plant according to claim 1, wherein said plant is homozygous for the introgression fragment and the plant is CVYV resistant.

5. A tetraploid watermelon plant made by doubling the chromosomes of the plant of claim 4.

6. The tetraploid watermelon plant according to claim 5, wherein the plant is an inbred line.

7. Seed from which a plant of claim 1 can be grown.

8. A vegetative propagation of a plant according to claim 1.

9. A cell or tissue culture of a plant of according to claim 1, wherein the cells or tissues comprise the introgression fragment.

10. The cell or tissue culture according to claim 9, comprising cells or protoplasts or plant tissue from a plant part, wherein the plant part is a scion, fruit, embryo, meristem, cotyledon, pollen, ovule, leaf, anther, root, root tip, pistil, flower, seed, or stem.

11. The plant part according to claim 1, wherein said part is a scion, fruit, pollen, ovule, stem, cotyledon, leaf, cell, embryo, meristem, anther, root, root tip, pistil, flower, or seed, and wherein the cells of said plant part comprise the introgression fragment.

12. A watermelon plant regenerated from the cell or tissue culture of claim 9.

13. A method for screening watermelon seeds, plants or plant parts or DNA from such seeds, plants or plant parts for the presence of one or more markers linked to CVYV resistance on chromosome 3, comprising detecting the presence of:
  a) a Guanine (G) at nucleotide 76 of SEQ ID NO: 2 (SNP_02); and
  b) a Cytosine (C) at nucleotide 76 of SEQ ID NO: 3 (SNP_03),
and selecting one or more seeds, plants or plant parts comprising a Guanine (G) at nucleotide 76 of SEQ ID NO: 2 (SNP 02) and a Cytosine (C) at nucleotide 76 of SEQ ID NO: 3 (SNP 03).

14. A method for producing triploid hybrid watermelon seeds, wherein plants grown from such seeds are CVYV resistant, comprising:
  a) allowing pollination of flowers of the tetraploid plant according to claim 5 with pollen of a diploid plant, and
  b) harvesting seeds produced in the fruits of the tetraploid plant,
wherein the diploid plant is a diploid cultivated watermelon plant of the species Citrullus lanatus ssp. vulgaris comprising an introgression fragment from a wild watermelon plant on chromosome 3 in homozygous form, whereby said introgression fragment comprises a CVYV-resistance conferring locus and whereby the introgression fragment comprises of the following markers:
  i) a Guanine (G) at nucleotide 76 of SEQ ID NO: 2 (SNP_02); and
  ii) a Cytosine (C) at nucleotide 76 of SEQ ID NO: 3 (SNP_03),
wherein the CVYV resistance conferring locus is obtainable from seeds deposited under accession number NCIMB42449, NCIMB42450, NCIMB42666, or from wild accession PI189318.

15. A triploid watermelon seed made by the method of claim 14.

16. A triploid plant grown from the seed of claim 15.

17. A method for seedless triploid watermelon fruit production comprising:
  (a) interplanting triploid hybrid seeds according to claim 15 with diploid pollenizer plants, and optionally
  (b) harvesting the seedless watermelon fruits produced on the triploid plants of (a).

18. A method for seedless triploid watermelon fruit production comprising:
  (a) interplanting triploid hybrid plants according to claim 16 with diploid pollenizer plants, and optionally
  (b) harvesting the seedless watermelon fruits produced on the triploid plants of (a).

19. A method for generating a diploid cultivated watermelon plant of the species Citrullus lanatus ssp. vulgaris, or part thereof, comprising an introgression fragment from wild watermelon plant on chromosome 3, whereby said introgression fragment comprises a CVYV-resistance conferring locus, comprising backcrossing a CVYV-resistance conferring locus from a wild watermelon plant comprising a Guanine (G) at nucleotide 76 of SEQ ID NO: 2 (SNP_02) and a Cytosine (C) at nucleotide 76 of SEQ ID NO: 3 (SNP_03) into a diploid cultivated watermelon plant and selecting progeny comprising a Guanine (G) at nucleotide 76 of SEQ ID NO: 2 (SNP_02) and a Cytosine (C) at nucleotide 76 of SEQ ID NO: 3 (SNP_03), and which are CVYV resistant in a CVYV resistance assay.

20. The method according to claim 19, wherein the wild watermelon plant is PI189318.

21. A method for generating a diploid cultivated watermelon plant of the species Citrullus lanatus ssp. vulgaris, or part thereof, comprising an introgression fragment from a wild Citrullus lanatus ssp. lanatus or a wild Citrullus lanatus ssp. mucospermus plant on chromosome 3, whereby said introgression fragment comprises a CVYV-resistance conferring locus, comprising backcrossing a CVYV-resistance conferring locus from the wild Citrullus lanatus ssp. lanatus or a wild Citrullus lanatus ssp. mucospermus plant comprising a Guanine (G) at nucleotide 76 of SEQ ID NO: 2 (SNP_02) and a Cytosine (C) at nucleotide 76 of SEQ ID NO: 3 (SNP_03) into a diploid cultivated watermelon plant and selecting progeny comprising a Guanine (G) at nucleotide 76 of SEQ ID NO: 2 (SNP_02) and a Cytosine (C) at nucleotide 76 of SEQ ID NO: 3 (SNP_03).

22. The method according to claim 21, wherein the introgression fragment from a wild Citrullus lanatus ssp. lanatus is obtainable from seeds deposited under accession number NCIMB42449 or NCIMB42450, and the introgression fragment from a wild Citrullus lanatus ssp. mucospermus is obtainable from NCIMB42666.

23. The plant according to claim 1, wherein the introgression fragment further comprises a Guanine (G) or an Adenine (A) at nucleotide 76 of SEQ ID NO: 1 (SNP_01).

* * * * *